US011634429B2

(12) United States Patent
Elder et al.

(10) Patent No.: US 11,634,429 B2
(45) Date of Patent: Apr. 25, 2023

(54) ORGANIC ELECTRO-OPTIC CHROMOPHORES

(71) Applicant: University of Washington, Seattle, WA (US)

(72) Inventors: Delwin Elder, Seattle, WA (US); Lewis Johnson, Seattle, WA (US); Bruce Robinson, Seattle, WA (US); Huajun Xu, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 17/713,055

(22) Filed: Apr. 4, 2022

(65) Prior Publication Data

US 2022/0227783 A1 Jul. 21, 2022

Related U.S. Application Data

(63) Continuation of application No. PCT/US2020/054081, filed on Oct. 2, 2020.

(60) Provisional application No. 62/934,398, filed on Nov. 12, 2019, provisional application No. 62/911,067, filed on Oct. 4, 2019.

(51) Int. Cl.
*C07D 495/04* (2006.01)
*C07D 307/28* (2006.01)
*C07F 7/08* (2006.01)
*G02F 1/361* (2006.01)
*H01L 51/00* (2006.01)

(52) U.S. Cl.
CPC ......... *C07D 495/04* (2013.01); *C07D 307/28* (2013.01); *C07F 7/0812* (2013.01); *G02F 1/3613* (2013.01); *G02F 1/3614* (2013.01); *H01L 51/0061* (2013.01); *H01L 51/0068* (2013.01); *H01L 51/0074* (2013.01); *H01L 51/0094* (2013.01)

(58) Field of Classification Search
CPC .................................................. C07D 495/04
See application file for complete search history.

(56) References Cited

U.S. PATENT DOCUMENTS

| 8,173,045 | B2 | 5/2012 | Jen | |
|---|---|---|---|---|
| 2002/0084446 | A1 | 7/2002 | Dalton | |
| 2007/0073034 | A1 | 3/2007 | Wang | |
| 2009/0118521 | A1* | 5/2009 | Jen | C07D 307/56 427/457 |
| 2011/0077408 | A1 | 3/2011 | Velusamy | |
| 2011/0111515 | A1 | 5/2011 | Nagano | |
| 2012/0252995 | A1 | 10/2012 | Jen | |
| 2012/0301828 | A1 | 11/2012 | Tachibana | |

FOREIGN PATENT DOCUMENTS

| CN | 103373990 | 10/2013 |
|---|---|---|
| CN | 103664843 | 3/2014 |
| CN | 103664933 | 3/2014 |
| CN | 103834000 | 6/2014 |
| CN | 104744896 | 7/2015 |
| CN | 109293643 | 2/2019 |
| CN | 109438459 | 3/2019 |
| EP | 2003488 | 12/2008 |
| KR | 20030027900 | 4/2003 |
| TW | 200563 | 2/1993 |
| WO | 2004065615 | 8/2004 |
| WO | 2015012456 | 1/2015 |
| WO | WO 2015012456 | * 1/2015 |

OTHER PUBLICATIONS

Cheng, Chem. Mater. 2007, 19, 1154-1163.*
Davies, J.A., et al., "Rational Enchancement of Second-Order Nonlinearity: Bis-(40methoxyphenyl) hetero-aryl-amino Donor-Based Chromophores: Design, Synthesis, and Elctrooptic Activitiy," Department of Chemistry, University of Washington, Jul. 19, 2008, 11 pages.
Deng, G., et al., "Synthesis and properties study of a novel nonlinear optical chromophore containing benzo[b]furan moiety based on julolidine," Journal of Molecular Structure, 2019, 439-443.
Fominykh, O.D., et al., "Composite materials containing chromophores with 3,7-(di)vinylquinoxalinone π-electron bridge doped into PMMA: Atomistic modeling and measurements of quadratic nonlinear optical activity," Arbuzov Institute of Organic and Physical Chemistry, 2018, 131-141.
Guo, Z , et al., "Synthesis of Novel Chromophore Based on Tricyanocyclopentenone Acceptor and Its NLO Property," Polycyclic Aromatic Compounds, 40(4): 1028-1035, 2020.
Hu, C., et al., "Synthesis and characterization of a novel indoline based nonlinear optical chromophore with excellent electro-optic activity and high thermal stability by modifying the p-conjugated bridges," Journal of Materials Chemistry C., 2017, 8 pages.
Jenner, M.O., "Synthesis of Organic Chromophores for use in Electro-Optic Polymers," University of Southampton, Dec. 2018, 82 pages.
Jin, W., et al., "Benzocyclobutene barrier layer for suppressing conductance in nonlinear optical devices during electric field poling," Appl. Phys. Lett. 104, Mar. 2014, 6 pages.
Liu, J., et al., "Progress in the enhancement of electro-optic coefficients and orientation stability for organic second-order nonlinear optical materials," Chinese Academy of Agricultural Sciences, Apr. 2020, 27 pages.
Liu, F., et al., "Using phenoxazine and phenothiazine as electron donors for secondorder nonlinear optical chromophore: Enhanced electro-optic activity," Technical Institute of Physics and Chemistry, 2015, pp. 196-203.

(Continued)

*Primary Examiner* — Nizal S Chandrakumar
(74) *Attorney, Agent, or Firm* — Christenson O'Connor Johnson Kindness PLLC

(57) ABSTRACT

Chromophores with large hyperpolarizabilities, films with electro-optic activity comprising the chromophores, and electro-optic devices comprising the chromophores are disclosed.

5 Claims, 8 Drawing Sheets

(56) References Cited

OTHER PUBLICATIONS

Luo, J., et al., "Facile Synthesis of Highly Efficient Phenyltetraene-Based Nonlinear Optical Chromophores for Electrooptics," Department of Materials Science & Engineering and Department of Chemistry, 8(7): 1387-1390, 2006.

Panunzi, B., et al., "A new donor-acceptor crosslinkable l-shape chromophore for NLO applications," Journal of Molecular Structure, 2019, pp. 21-27.

Wang, L-D., et al., "Synthesis and characterization of electron-optic polyurethane-imide and fabrication of optical waveguide device," High Performance Polymers, 29(8): 879-888, 2017.

Wu, J., et al., "Synthesis of novel nonlinear optical chromophore to achieve ultrahigh alectro-optic activity," Chem Commun., 2012, 48, 9637-9639.

Xu, H., et al., "Nonlinear optical chromophores based on Dewar's rules: enhancement of electro-optic activity by ntroducing heteroatoms into thedonoror bridge," Phys. Chem. Chem Phys., 2015, pp. 1-10.

Xu, H., et al., "Novel second-order nonlinear optical chromophores containing multiheteroatoms in donor moiety Design, synthesis, DFT studies and electro-optic activities," Technical Institute of Physics and Chemistry, 2014, 142-149.

Yang, Y., et al., "A novel chromophore containing a Michler's donor and a tricyanofuran acceptor with enhanced nonlinear optical properties," Technical Institute of Physics and Chemistry, 2019, pp. 1-3.

Yang, Y., et al., "Enhanced electro-optic activity and thermal stability by introducing rigid steric hindrance groups into double-donor chromophore," Technical Institute of Physics and Chemistry, 2018, 222-229.

Yang, Y., et al., "Enhanced electro-optic activity from the triarylaminophenyl-based chromophores by introducing heteroatoms to the donor," Journal of Materials of Chemistry C., 2015, pp. 1-10.

Yang, Y., et al., "Using phenothiazine as electron donor for new second-order nonlinear optical chromophore," Technical Institute of Physics and Chemistry, 2019, 196-199.

\* cited by examiner

ORGANIC ELECTRO-OPTIC CHROMOPHORES

CROSS-REFERENCES TO RELATED APPLICATIONS

This application is a continuation of International Application No. PCT/US2020/054081, filed Oct. 2, 2020, which claims the benefit of U.S. Provisional Application 62/911,067, filed Oct. 4, 2019, and U.S. Provisional Application 62/934,398, filed Nov. 12, 2019, the disclosures of which are incorporated herein by reference in their entirety.

STATEMENT OF GOVERNMENT LICENSE RIGHTS

This invention was invention was made with government support under Grant No. FA9550-15-1-0319, awarded by the Air Force Office of Scientific Research and Grant No. DMR1303080, awarded by the National Science Foundation. The government has certain rights in the invention.

FIELD OF THE INVENTION

The present disclosure provides chromophores useful for inclusion in films having electro-optic activity and electro-optic devices.

BACKGROUND

Organic electro-optic (OEO) materials have recently seen a resurgence in interest due to the development of silicon-organic hybrid (SOH) and plasmonic-organic hybrid (POH) devices, which enable combining the high intrinsic electro-optic activity of certain classes of organic chromophores with small device size and potential for chip-scale integration with CMOS electronics. The size of electro-optic devices is proportional to the voltage-length product $U_\pi L \propto 1/n^3 r_{33}$, where $U_\pi$ is the voltage required to induce a phase shift of $\pi$ over a path length L, n is the refractive index of the electro-optic material, and $r_{33}$ is the electro-optic coefficient of the material. In an OEO material, $r_{33} \propto \rho_N \beta \langle \cos^3\theta \rangle$, where $\rho_N$ is the number density (concentration) of chromophores that possess a large molecular hyperpolarizability ($\beta$), and have been aligned such that their dipole moments are acentrically ordered (nonzero $\langle \cos^3\theta \rangle$, where $\theta$ is the angle between the dipole moments of the chromophores and the axis normal to the electrodes of the electro-optic device.

High hyperpolarizability chromophores typically have a donor-$\pi$ bridge-acceptor (D-$\pi$-A) structure, containing an electron donating moiety such as a substituted amine group, an electron-accepting moiety containing strong electron-withdrawing groups such as cyano (CN) or nitro (NO$_2$), connected by a $\pi$-conjugated linker, often containing ene/polyene and/or heteroaromatic groups, such as a D-$\pi$-A chromophore, known as JRD1 depicted in FIG. 1.

A need exists for chromophores having higher chromophore hyperpolarizabilities and favorable stability and processability, enabling higher $r_{33}$ and smaller $U_\pi L$ in devices for any given chromophore concentration.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides a compound of Formula A:

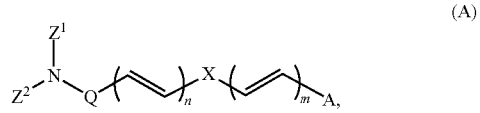

(A)

wherein:
A is an $\pi$-electron acceptor group;
X is:

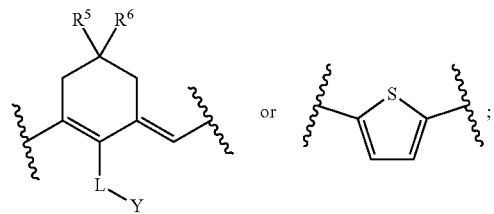

L is absent or L is S or O;
Y is H, optionally substituted C1-C20 alkyl, optionally substituted C3-C50 heteroalkyl, optionally substituted C3-C10 cycloalkyl, optionally substituted C3-C10 cycloheteroalkyl;
n is 1, 2, or 3;
n is 1, 2, or 3, and
$R^5$ and $R^6$ are independently H, optionally substituted C1-C10 alkyl, optionally substituted C3-C10 heteroalkyl, optionally substituted C3-C10 cycloalkyl, or optionally substituted C3-C10 cycloheteroalkyl;
Q is

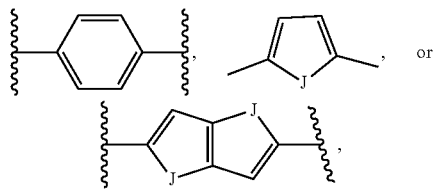

J, at each occasion, is independently S, O, or $NR^8$;
$R^8$ is H, optionally substituted C1-C10 alkyl, optionally substituted C3-C10 heteroalkyl, optionally substituted C3-C10 cycloalkyl, optionally substituted C3-C10 cycloheteroalkyl, optionally substituted C6-C10 aryl, or optionally substituted C5-C10 heteroaryl; and
when Q is

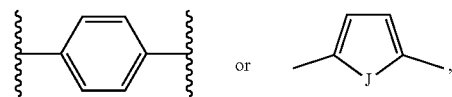

$Z^1$ is optionally substituted C6-C10 aryl, or optionally substituted C5-C10 heteroaryl and $Z^2$ is H, optionally substituted C1-C10 alkyl, optionally substituted C3-C10 heteroalkyl, optionally substituted C3-C10 cycloalkyl, optionally substituted C3-C10 cycloheteroalkyl, optionally substituted C6-C10 aryl, or optionally substituted C5-C10 heteroaryl or when Q is

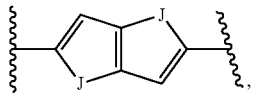

$Z^1$ and $Z^2$ are independently H, optionally substituted C1-C10 alkyl, optionally substituted C3-C10 heteroalkyl, optionally substituted C3-C10 cycloalkyl, optionally substituted C3-C10 cycloheteroalkyl, optionally substituted C6-C10 aryl, or optionally substituted C5-C10 heteroaryl.

In some embodiments, the compound is represented by Formula A1:

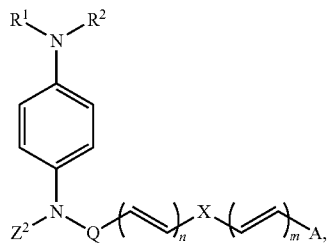

(A1)

wherein:

$Z^2$, Q, X, A, n, and m are as defined above; and $R^1$ and $R^2$ are independently H, optionally substituted C1-C10 alkyl, optionally substituted C3-C10 heteroalkyl, optionally substituted C3-C10 cycloalkyl, or optionally substituted C3-C10 cycloheteroalkyl.

In some embodiments, the compound is represented by Formula A2:

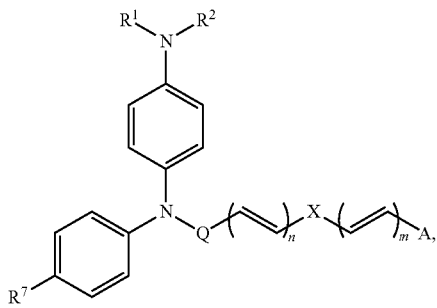

(A2)

wherein:

Q, X, A, n, and m are as defined above;

$R^1$ and $R^2$ are independently H, optionally substituted C1-C10 alkyl, optionally substituted C3-C10 heteroalkyl, optionally substituted C3-C10 cycloalkyl, or optionally substituted C3-C10 cycloheteroalkyl;

$R^7$ is H, optionally substituted C1-C10 alkyl, optionally substituted C3-C10 heteroalkyl, optionally substituted C3-C10 cycloalkyl, or optionally substituted C3-C10 cycloheteroalkyl, optionally substituted C1-C10 alkyloxy, optionally substituted C3-C10 heteroalkyloxy, or $NR^3R^4$; and $R^3$ and $R^4$ are independently H, optionally substituted C1-C10 alkyl, optionally substituted C3-C10 heteroalkyl, optionally substituted C3-C10 cycloalkyl, or optionally substituted C3-C10 cycloheteroalkyl.

In some embodiments, the compound is represented by Formula A3:

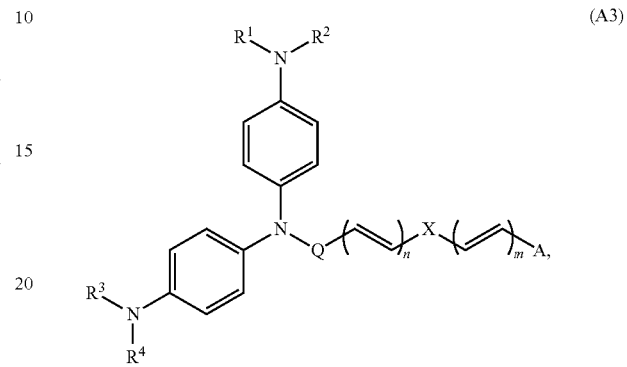

(A3)

wherein:

Q, X, A, n, and m are as defined above;

$R^1$ and $R^2$ are independently H, optionally substituted C1-C10 alkyl, optionally substituted C3-C10 heteroalkyl, optionally substituted C3-C10 cycloalkyl, or optionally substituted C3-C10 cycloheteroalkyl; and $R^3$ and $R^4$ are independently H, optionally substituted C1-C10 alkyl, optionally substituted C3-C10 heteroalkyl, optionally substituted C3-C10 cycloalkyl, or optionally substituted C3-C10 cycloheteroalkyl.

In some embodiments, the compound is represented by Formula A4:

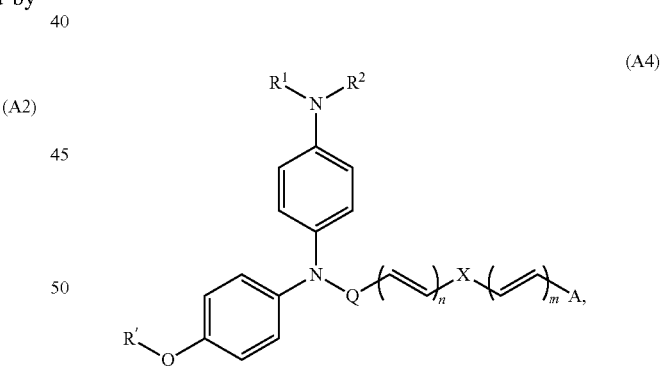

(A4)

wherein:

Q, X, A, n, and m are as defined above;

$R^1$ and $R^2$ are independently H, optionally substituted C1-C10 alkyl, optionally substituted C3-C10 heteroalkyl, optionally substituted C3-C10 cycloalkyl, or optionally substituted C3-C10 cycloheteroalkyl; and R' is optionally substituted C1-C10 alkyl, optionally substituted C3-C10 heteroalkyl, optionally substituted C3-C10 cycloalkyl, or optionally substituted C3-C10 cycloheteroalkyl.

In some embodiments, Q is:

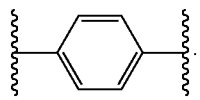

In some embodiments, Q is:

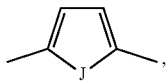

wherein J is i S, O, or NR$^8$; and R$^8$ is H, optionally substituted C1-C10 alkyl, optionally substituted C3-C10 heteroalkyl, optionally substituted C3-C10 cycloalkyl, optionally substituted C3-C10 cycloheteroalkyl, optionally substituted C6-C10 aryl, or optionally substituted C5-C10 heteroaryl.

In some embodiments, Q is:

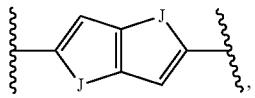

wherein J, at each occasion, is independently S, O, or NR$^8$; and

R$^8$ is H, optionally substituted C1-C10 alkyl, optionally substituted C3-C10 heteroalkyl, optionally substituted C3-C10 cycloalkyl, optionally substituted C3-C10 cycloheteroalkyl, optionally substituted C6-C10 aryl, or optionally substituted C5-C10 heteroaryl.

In some embodiments, J is S.

In some embodiments, A is

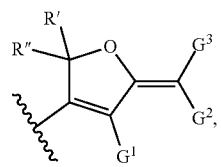

wherein R' and R" are independently selected from optionally substituted C1-C12 alkyl (e.g., fluorinated alkyl) and optionally substituted C6-C10 aryl (e.g., fluorinated aryl), and G$^1$, G$^2$, and G$^3$ are independently selected from F, CN, CF$_3$, SO$_2$CF$_3$.

In some embodiments, A is

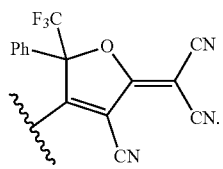 [SMILES: *C1=C(C#N)C(=C(C#N)C#N)OC1(c1ccccc1)C(F)(F)F]

In some embodiments, m is 1. In some embodiments, n is 1.

In some embodiments, the compound is a compound of Formula A5:

(A5)

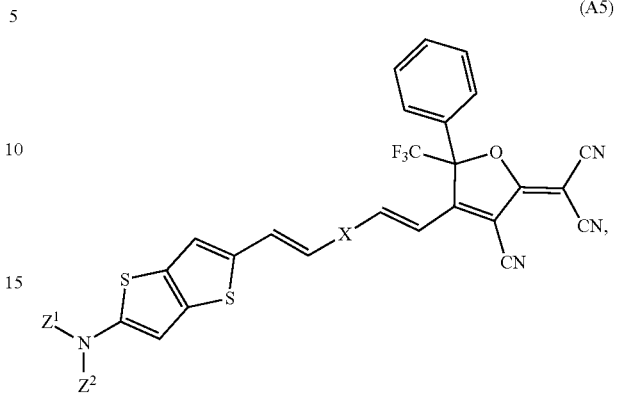

wherein:

Z$^1$ and Z$^2$ are independently H, optionally substituted C1-C10 alkyl, optionally substituted C3-C10 heteroalkyl, optionally substituted C3-C10 cycloalkyl, optionally substituted C3-C10 cycloheteroalkyl, optionally substituted C6-C10 aryl, or optionally substituted C5-C10 heteroaryl;

X is:

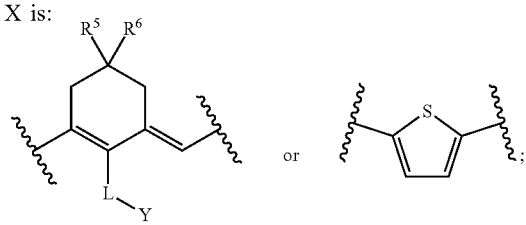

L is absent or L is S or O;

Y is H, optionally substituted C1-C20 alkyl, optionally substituted C3-C50 heteroalkyl, optionally substituted C3-C10 cycloalkyl, or optionally substituted C3-C10 cycloheteroalkyl; and R$^5$ and R$^6$ are independently H, optionally substituted C1-C10 alkyl, optionally substituted C3-C10 heteroalkyl, optionally substituted C3-C10 cycloalkyl, or optionally substituted C3-C10 cycloheteroalkyl.

In some embodiments, the compound is a compound of Formula A6:

(A6)

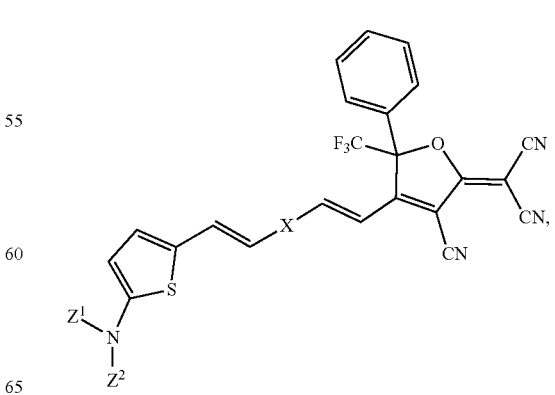

wherein:

$Z^1$ is optionally substituted C6-C10 aryl or optionally substituted C5-C10 heteroaryl;

$Z^2$ is H, optionally substituted C1-C10 alkyl, optionally substituted C3-C10 heteroalkyl, optionally substituted C3-C10 cycloalkyl, optionally substituted C3-C10 cycloheteroalkyl, optionally substituted C6-C10 aryl, or optionally substituted C5-C10 heteroaryl;

X is:

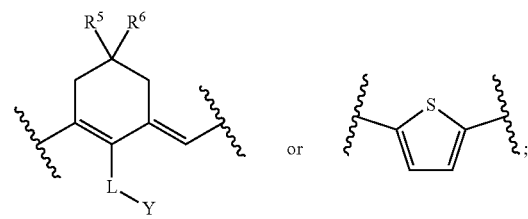

L is absent or L is S or O;

Y is H, optionally substituted C1-C20 alkyl, optionally substituted C3-C50 heteroalkyl, optionally substituted C3-C10 cycloalkyl, or optionally substituted C3-C10 cycloheteroalkyl; and $R^5$ and $R^6$ are independently H, optionally substituted C1-C10 alkyl, optionally substituted C3-C10 heteroalkyl, optionally substituted C3-C10 cycloalkyl, or optionally substituted C3-C10 cycloheteroalkyl.

In some embodiments, the compound is a compound of Formula A7:

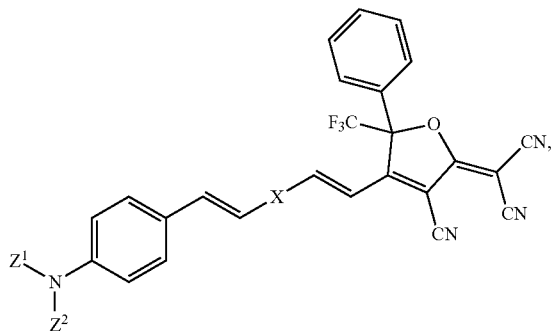

(A7)

wherein:

$Z^1$ is optionally substituted C6-C10 aryl or optionally substituted C5-C10 heteroaryl;

$Z^2$ is H, optionally substituted C1-C10 alkyl, optionally substituted C3-C10 heteroalkyl, optionally substituted C3-C10 cycloalkyl, optionally substituted C3-C10 cycloheteroalkyl, optionally substituted C6-C10 aryl, or optionally substituted C5-C10 heteroaryl;

X is:

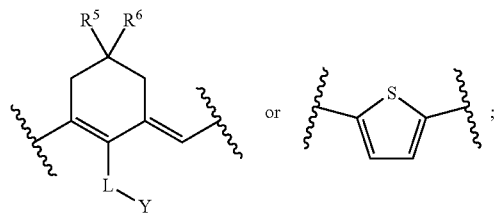

L is absent or L is S or O;

Y is H, optionally substituted C1-C20 alkyl, optionally substituted C3-C50 heteroalkyl, optionally substituted C3-C10 cycloalkyl, or optionally substituted C3-C10 cycloheteroalkyl; and $R^5$ and $R^6$ are independently H, optionally substituted C1-C10 alkyl, optionally substituted C3-C10 heteroalkyl, optionally substituted C3-C10 cycloalkyl, or optionally substituted C3-C10 cycloheteroalkyl.

In some embodiments, the compound comprises one or more reactive groups that can form a covalent bond when reacted with a counterpart reactive group. In some embodiments, the one or more reactive groups is a group cross-linkable by (4+2) cycloaddition.

In some embodiments, at least one of $Z^1$ and X is substituted with a group selected from

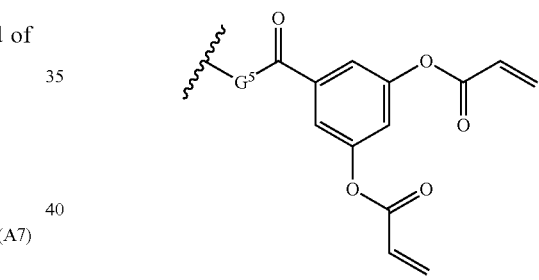

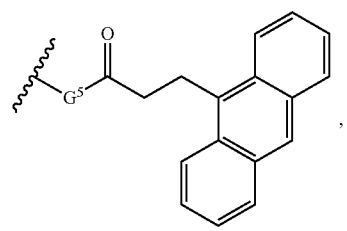

and $OSiR^{10}R^{11}R^{12}$, wherein $G^5$ is NH, O, S, or N(C1-C10-alkyl) and $R^{10}$, $R_{11}$, and $R^{12}$ are independently H, optionally substituted C1-C10 alkyl, or optionally substituted C6-C10 aryl.

In some embodiments, L-Y is H, $OL^1OSiR^{10}R^{11}R^{12}$, or $SL^1OSiR^{10}R^{11}R^{12}$, wherein $L^1$ is an optionally substituted C2-C20 alkylene or optionally substituted C3-C50 heteroalkylene; and $R^{10}$, $R_{11}$, and $R^{12}$ are independently H, optionally substituted C1-C10 alkyl, or optionally substituted C6-C10 aryl.

In some embodiments, X is:

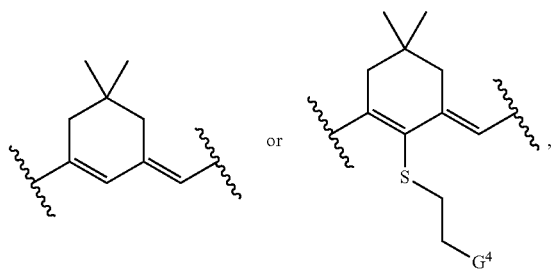

wherein $G^4$ is $OSiR^{10}R^{11}R^{12}$, wherein $R^{10}$, $R^{11}$, and $R^{12}$ are independently H, optionally substituted C1-C10 alkyl, or optionally substituted C6-C10 aryl, or $G^4$ is

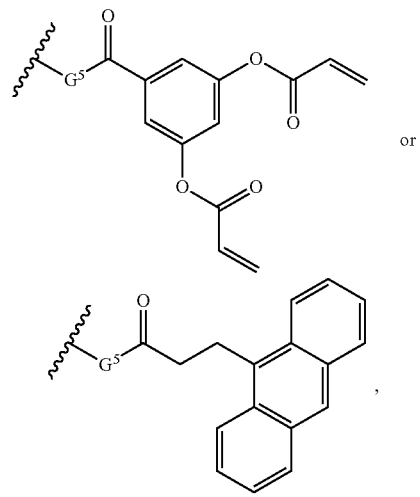

wherein $G^5$ is NH, O, S, or N(C1-C10-alkyl).

In some embodiments, the compound is a compound of Formula A8:

C3-C10 cycloalkyl, or optionally substituted C3-C10 cycloheteroalkyl; and

Y is optionally substituted C1-C10 alkyl, optionally substituted C3-C10 heteroalkyl, optionally substituted C3-C10 cycloalkyl, or optionally substituted C3-C10 cycloheteroalkyl; and wherein at least one of $R^2$, Y, and $G^6$ is substituted with a group selected from

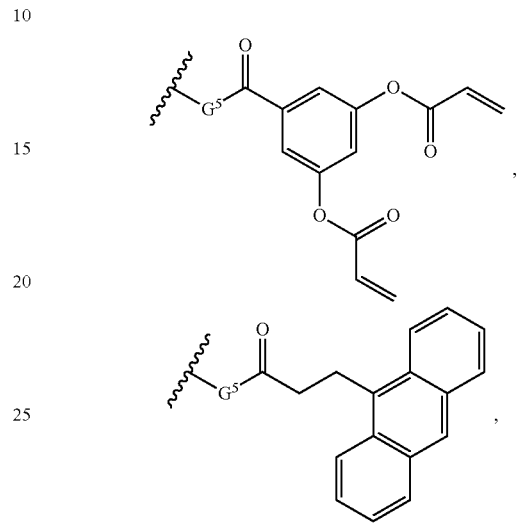

and $OSiR^{10}R^{11}R^{12}$, wherein $G^5$ is NH, O, S, or N(C1-C10-alkyl) and $R^{10}$, $R^{11}$, and $R^{12}$ are independently H, optionally substituted C1-C10 alkyl, or optionally substituted C6-C10 aryl.

In some embodiments, the compound is Compound I, Compound II, Compound III, or Compound IV, Compound V, Compound VI, Compound VII, Compound VIII, Compound IX, Compound X, Compound XI, Compound XII, Compound XIII, Compound XIV, or Compound XV depicted below.

(A8)

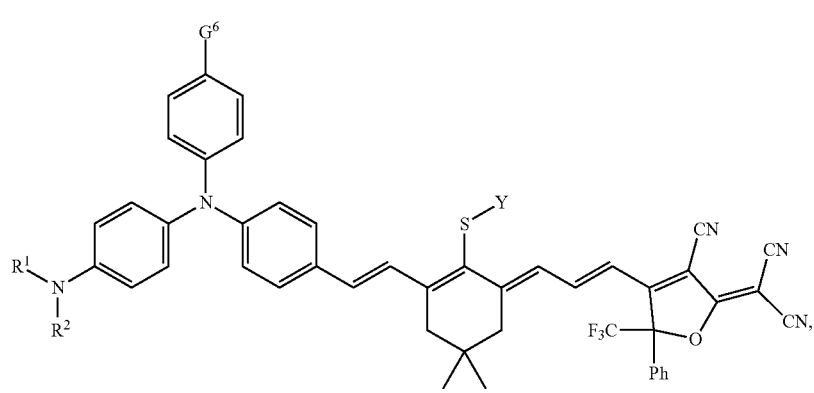

wherein:

$G^6$ is OR' or NR'R", wherein R' and R" are independently optionally substituted C1-C10 alkyl;

$R^1$ is H or an optionally substituted C1-C10 alkyl, $R^2$ is optionally substituted C1-C10 alkyl, optionally substituted C3-C10 heteroalkyl, optionally substituted In another aspect, the disclosure provides a film having electro-optic activity comprising one or more compounds disclosed herein. In some embodiments, the film further comprises a polymer. In some embodiments, the polymer is polymethylmethacrylate (PMMA). In some embodiments, the film has an $r_{33}$ value of greater than about 100 pm/V. In some embodiments, the film has an $r_{33}$ value of greater than about 1000 pm/V. In some embodiments, the film has a $T_g$ of about 105° C. or greater.

In another aspect, the disclosure provides a method for forming a film having electro-optic activity, comprising depositing a compound or mixture containing a compound of disclosed herein on a substrate to provide a film, applying an aligning force to the film at a temperature sufficient to provide a film having at least a portion of the compounds aligned, and reducing the temperature of the film to provide a film having electro-optic activity.

In another aspect, the disclosure provides an electro-optic device comprising a compound of disclosed herein.

In another aspect, the disclosure provides an electro-optic device comprising a film disclosed herein.

In some embodiments, the electro-optic device further comprises one or more charge blocking layers. In some embodiments, the one or more charge blocking layers comprises poly(benzocyclobutene) (BCB), $TiO_2$, $MoO_3$, $ZrO_2$, $HfO_2$, $SiO_2$, $Al_2O_3$, $Si_3N_4$, or a combination thereof. In some embodiments, the device is an electro-optic modulator, antenna, Mach-Zehnder modulator, phase modulator, silicon-organic hybrid modulator, plasmonic-organic hybrid modulator, electrical-to-optical convertor, terahertz detector, frequency shifter, or frequency comb source.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
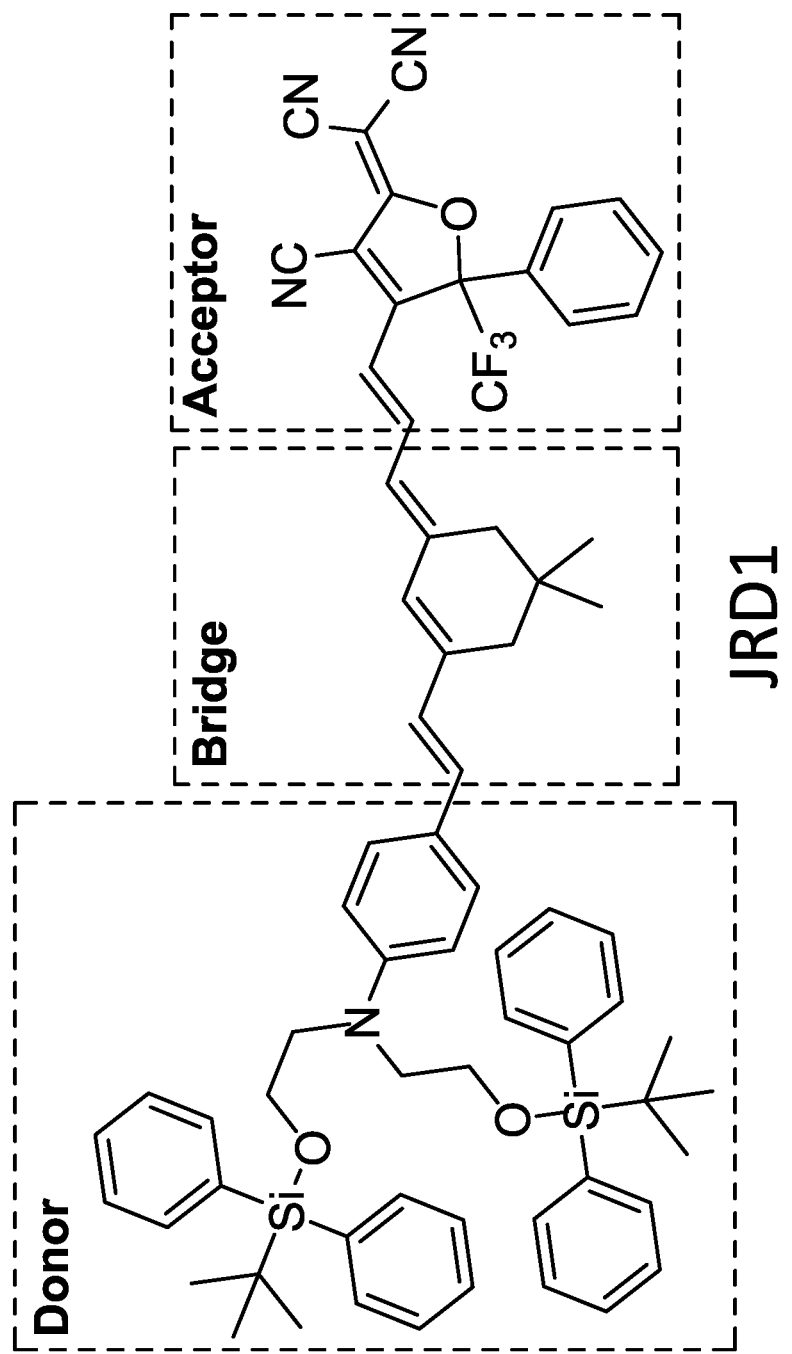
FIG. 1 depicts known JRD1 chromophore, with donor, π-bridge, and acceptor labeled. JRD1 contains a substituted aniline donor, a ring-locked polyene bridge, and a $CF_3$-phenyl substituted tricyanofuran (TCF) acceptor

Provided herein are chromophores with large hyperpolarizabilities, films with electro-optic activity comprising the chromophores, and electro-optic devices comprising the chromophores. The chromophores of the disclosure possess a large molecular hyperpolarizability, which enables a large electro-optic coefficient ($r_{33}$) in films containing the chromophores.

The polarizable chromophore compounds or polarizable chromophores disclosed herein are second-order nonlinear optical chromophore compounds. As used herein, the term "chromophore" refers to a compound that can absorb light in the visible spectral range and is colored. The terms "polarizable chromophore compound," "polarizable chromophore," and "chromophore" are used interchangeably throughout the disclosure, unless indicated otherwise. In the context of the disclosure, the term "nonlinear" refers second order effects that arise from the nature of the polarizable chromophore compound (i.e., "push-pull" chromophore compound) having the general structure D-π-A, where D is an electron donor, A is an electron acceptor, and π is a π-bridge that conjugates the donor to the acceptor.

A "donor" (represented by "D") is an atom or group of atoms with low electron affinity relative to an acceptor (defined below) such that, when the donor is conjugated to an acceptor through a π-bridge, electron density is transferred from the donor to the acceptor.

An "acceptor" (represented by "A") is an atom or group of atoms with high electron affinity relative to a donor such that, when the acceptor is conjugated to a donor through a π-bridge, electron density is transferred from the acceptor to the donor.

A "π-bridge" or "conjugated bridge" (represented in chemical structures by "π" or "$\pi_n$," where n is an integer) is comprised of an atom or group of atoms through which electrons can be delocalized from an electron donor (defined above) to an electron acceptor (defined above) through the orbitals of atoms in the bridge. Preferably, the orbitals will be p-orbitals on multiply bonded carbon atoms such as those found in alkenes, alkynes, neutral or charged aromatic rings, and neutral or charged heteroaromatic ring systems. Additionally, the orbitals can be p-orbitals on multiply bonded atoms such as boron or nitrogen or organometallic orbitals. The atoms of the bridge that contain the orbitals through which the electrons are delocalized are referred to here as the "critical atoms." The number of critical atoms in a bridge can be a number from 1 to about 30. The critical atoms can also be substituted further with the following: "alkyl" as defined below, "aryl" as defined below, or "heteroalkyl" as defined below. One or more atoms, with the exception of hydrogen, on alkyl, aryl, or heteroalkyl substituents of critical atoms in the bridge may be bonded to atoms in other alkyl, aryl, or heteroalkyl substituents to form one or more rings.

In one aspect, provided herein are polarizable chromophore compounds of Formula A:

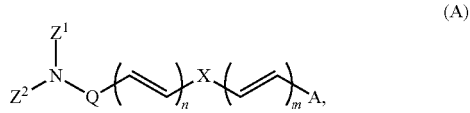

(A)

wherein:

A is a π-electron acceptor group;

$Z^1$ and $Z^2$ are independently H, optionally substituted $C_1$-$C_{10}$ alkyl, optionally substituted $C_3$-$C_{10}$ heteroalkyl, optionally substituted $C_3$-$C_{10}$ cycloalkyl, optionally substituted $C_3$-$C_{10}$ cycloheteroalkyl, optionally substituted $C_6$-$C_{10}$ aryl, or optionally substituted $C_5$-$C_{10}$ heteroaryl;

Q is

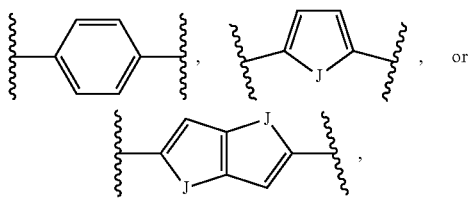

J, at each occasion, is independently S, O, or $NR^8$;

$R^8$ is H, optionally substituted $C_1$-$C_{10}$ alkyl, optionally substituted $C_3$-$C_{10}$ heteroalkyl, optionally substituted $C_3$-$C_{10}$ cycloalkyl, optionally substituted $C_3$-$C_{10}$ cycloheteroalkyl, optionally substituted $C_6$-$C_{10}$ aryl, or optionally substituted $C_5$-$C_{10}$ heteroaryl;

X is:

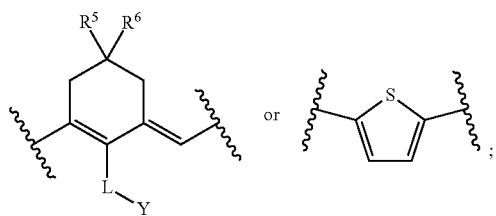

L is absent or L is S or O;

Y is H, optionally substituted $C_1$-$C_{20}$ alkyl, optionally substituted $C_3$-$C_{50}$ heteroalkyl, optionally substituted $C_3$-$C_{10}$ cycloalkyl, or optionally substituted $C_3$-$C_{10}$ cycloheteroalkyl;

n is 1, 2, or 3;

n is 1, 2, or 3; and $R^5$ and $R^6$ are independently H, optionally substituted $C_1$-$C_{10}$ alkyl, optionally substituted $C_3$-$C_{10}$ heteroalkyl, optionally substituted $C_3$-$C_{10}$ cycloalkyl, or optionally substituted $C_3$-$C_{10}$ cycloheteroalkyl, provided that when when Q is

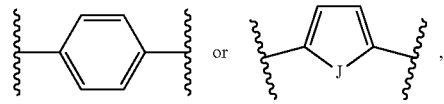

$Z^1$ is optionally substituted $C_6$-$C_{10}$ aryl or optionally substituted $C_5$-$C_{10}$ heteroaryl and $Z^2$ is H, optionally substituted $C_1$-$C_{10}$ alkyl, optionally substituted $C_3$-$C_{10}$ heteroalkyl, optionally substituted $C_3$-$C_{10}$ cycloalkyl, optionally substituted $C_3$-$C_{10}$ cycloheteroalkyl, optionally substituted $C_6$-$C_{10}$ aryl, or optionally substituted $C_5$-$C_{10}$ heteroaryl, and when Q is

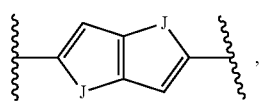

$Z^1$ and $Z^2$ are independently H, optionally substituted $C_1$-$C_{10}$ alkyl, optionally substituted $C_3$-$C_{10}$ heteroalkyl, optionally substituted $C_3$-$C_{10}$ cycloalkyl, optionally substituted $C_3$-$C_{10}$ cycloheteroalkyl, optionally substituted $C_6$-$C_{10}$ aryl, or optionally substituted $C_5$-$C_{10}$ heteroaryl.

As used herein, the terms "alkyl," "alkenyl," and "alkynyl" include straight-chain, branched-chain, and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C, as $C_1$-$C_{10}$, C-C10, or C1-10.

The terms "heteroalkyl," "heteroalkenyl," and "heteroalkynyl," as used herein, mean the corresponding hydrocarbons wherein one or more chain carbon atoms have been replaced by a heteroatom. Exemplary heteroatoms include N, O, S, and P. When heteroatoms are allowed to replace carbon atoms, for example, in heteroalkyl groups, the numbers describing the group, though still written as e.g. C3-C10, represent the sum of the number of carbon atoms in the cycle or chain and the number of such heteroatoms that are included as replacements for carbon atoms in the cycle or chain being described.

Typically, the alkyl, alkenyl, and alkynyl substituents contain 1-20 carbon atoms (alkyl) or 2-10 carbon atoms (alkenyl or alkynyl). Preferably, they contain 1-10 carbon atoms (alkyl) or 2-10 carbon atoms (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond. As used herein, the terms "cycloalkyl," "cycloalkenyl," and "cycloalkynyl" specifically refer to cyclic alkyls, alkenyls, and alkynyls, respectively.

As used herein, the terms "alkylene," "alkenylene," and "alkynylene" can include straight-chain, branched-chain, and cyclic divalent hydrocarbyl radicals, and combinations thereof. As used herein, the terms "cycloalkylene," "cycloalkenylene," and "cycloalkynylene" specifically refer to cyclic divalent hydrocarbyl radicals.

Alkyl, alkenyl, and alkynyl groups can be optionally substituted to the extent that such substitution makes sense chemically. Typical substituents include, but are not limited to, halogens (F, Cl, Br, I), =O, =N—CN, =N—OR, =NR, OR, $NR_2$, SR, $SO_2R$, $SO_2NR_2$, $NRSO_2R$, $NRCONR_2$, NRC(O)OR, NRC(O)R, CN, C(O)OR, C(O)$NR_2$, OC(O)R, C(O)R, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halogens (F, Cl, Br, I), =O, =N—CN, =N—OR', =NR', OR', NR'$_2$, SR', $SO_2R'$, $SO_2NR'_2$, NR'$SO_2R'$, NR'CONR'$_2$, NR'C(O)OR', NR'C(O)R', CN, C(O)OR', C(O)NR'$_2$, OC(O) R', C(O)R', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl, and alkynyl groups can also be substituted by C1-C8 acyl, C2-C8 heteroacyl, C6-C10 aryl or C5-C10 heteroaryl, each of which can be substituted by the substituents that are appropriate for the particular group.

While "alkyl" as used herein includes cycloalkyl and cycloalkylalkyl groups, the term "cycloalkyl" is used herein to describe a carbocyclic non-aromatic group that is connected via a ring carbon atom, and "cycloalkylalkyl" is used to describe a carbocyclic non-aromatic group that is connected to the molecule through an alkyl linker. Similarly, "heterocyclyl" is used to identify a non-aromatic cyclic group that contains at least one heteroatom as a ring member and that is connected to the molecule via a ring atom, which may be C or N; and "heterocyclylalkyl" may be used to describe such a group that is connected to another molecule through an alkylene linker. As used herein, these terms also include rings that contain a double bond or two, as long as the ring is not aromatic.

"Aromatic" or "aryl" substituent or moiety refers to a monocyclic or fused bicyclic moiety having the well-known characteristics of aromaticity; examples include phenyl and naphthyl. Similarly, the terms "heteroaromatic" and "heteroaryl" refer to such monocyclic or fused bicyclic ring systems which contain as ring members one or more heteroatoms. Suitable heteroatoms include N, O, and S, inclusion of which permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl, and fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably, the monocyclic heteroaryls contain 5-6 ring members, and the bicyclic heteroaryls contain 8-10 ring members.

Aryl and heteroaryl moieties can be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halogens (F, Cl, Br, I), OR, $NR_2$, SR, $SO_2R$, $SO_2NR_2$, $NRSO_2R$, $NRCONR_2$, NRC(O)OR, NRC(O)R, CN, C(O)OR, $C(O)NR_2$, OC(O)R, C(O)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

"Optionally substituted," as used herein, indicates that the particular group being described may have one or more hydrogen substituents replaced by a non-hydrogen substituent. In some optionally substituted groups or moieties, all hydrogen substituents are replaced by a non-hydrogen substituent, e.g., C1-C6 alkyl, C2-C6 heteroalkyl, alkynyl, halogens (F, Cl, Br, I), $N_3$, OR, $NR_2$, $SiR_3$, $OSiR_3$, SR, $SO_2R$, $SO_2NR_2$, $NRSO_2R$, $NRCONR_2$, NRC(O)OR, NRC(O)R, CN, C(O)OR, $C(O)NR_2$, OC(O)R, C(O)R, oxo, and $NO_2$, wherein each R is independently H, C1-C6 alkyl, C6-C10 aryl, or C2-C6 heteroalkyl. Where an optional substituent is attached via a double bond, such as a carbonyl oxygen or oxo (=O), the group takes up two available valences, so the total number of substituents that may be included is reduced according to the number of available valences. In some embodiments, the optional non-hydrogen substituent is OSiRR'R", wherein R, R', and R' are independently H, C1-C10 alkyl, or C6-C10 aryl.

In some embodiments, optional substituents include reactive groups such as groups crosslinkable by (4+2) cycloaddition, for example,

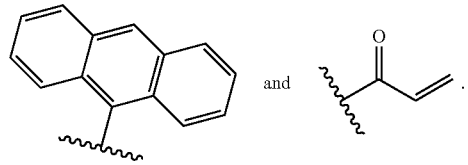

In some embodiments of Formula A, one or more of $Z^1$, $Z^2$, Q, X, and A can be optionally substituted with one or more reactive groups such as groups crosslinkable by (4+2) cycloaddition described above.

In some embodiments of Formula A, the compound is represented by Formula A1:

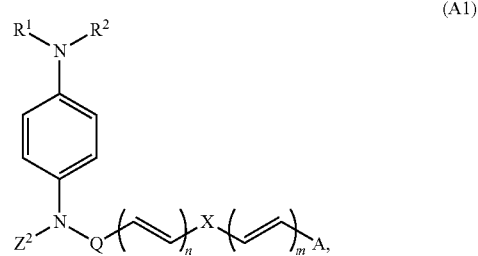

(A1)

wherein:

$Z^2$, Q, X, A, n, and m are as defined above for Compound of Formula A; and $R^1$ and $R^2$ are independently H, optionally substituted $C_1$-$C_{10}$ alkyl, optionally substituted $C_3$-$C_{10}$ heteroalkyl, optionally substituted $C_3$-$C_{10}$ cycloalkyl, or optionally substituted $C_3$-$C_{10}$ cycloheteroalkyl.

In some embodiments, the compound is represented by Formula A2:

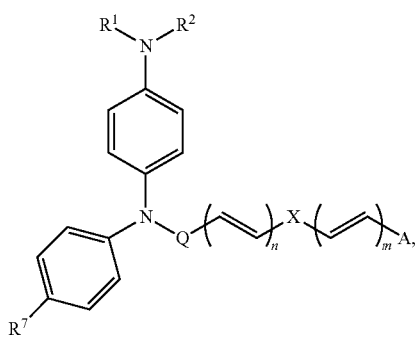

(A2)

wherein:

Q, X, A, n, and m are as defined above;

$R^1$ and $R^2$ are independently H, optionally substituted $C_1$-$C_{10}$ alkyl, optionally substituted $C_3$-$C_{10}$ heteroalkyl, optionally substituted $C_3$-$C_{10}$ cycloalkyl, or optionally substituted $C_3$-$C_{10}$ cycloheteroalkyl;

$R^7$ is H, optionally substituted $C_1$-$C_{10}$ alkyl, optionally substituted $C_3$-$C_{10}$ heteroalkyl, optionally substituted $C_3$-$C_{10}$ cycloalkyl, or optionally substituted $C_3$-$C_{10}$ cycloheteroalkyl, optionally substituted $C_1$-$C_{10}$ alkyloxy, optionally substituted $C_3$-$C_{10}$ heteroalkyloxy, or $NR^3R^4$; and $R^3$ and $R^4$ are independently H, optionally substituted $C_1$-$C_{10}$ alkyl, optionally substituted $C_3$-$C_{10}$ heteroalkyl, optionally substituted $C_3$-$C_{10}$ cycloalkyl, or optionally substituted $C_3$-$C_{10}$ cycloheteroalkyl.

In some embodiments, the compound is represented by Formula A3:

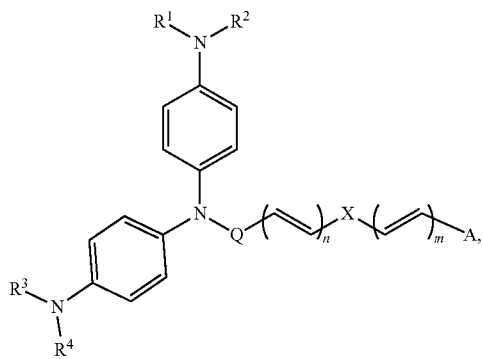

(A3)

wherein:

Q, X, A, n, and m are as defined above;

$R^1$ and $R^2$ are independently H, optionally substituted $C_1$-$C_{10}$ alkyl, optionally substituted $C_3$-$C_{10}$ heteroalkyl, optionally substituted $C_3$-$C_{10}$ cycloalkyl, or optionally substituted $C_3$-$C_{10}$ cycloheteroalkyl; and $R^3$ and $R^4$ are independently H, optionally substituted $C_1$-$C_{10}$ alkyl, optionally substituted $C_3$-$C_{10}$ heteroalkyl, optionally substituted $C_3$-$C_{10}$ cycloalkyl, or optionally substituted $C_3$-$C_{10}$ cycloheteroalkyl.

In some embodiments, the compound is represented by Formula A4:

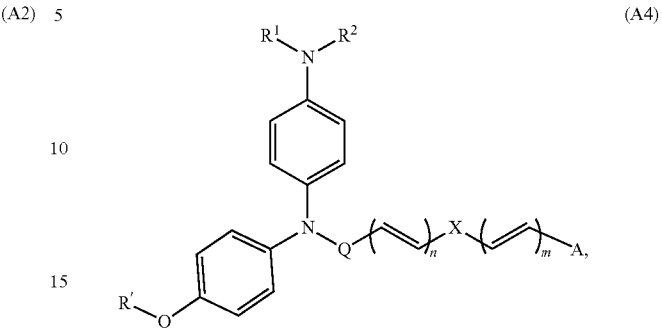

(A4)

wherein:

Q, X, A, n, and m are as defined above for Compound A;

$R^1$ and $R^2$ are independently H, optionally substituted $C_1$-$C_{10}$ alkyl, optionally substituted $C_3$-$C_{10}$ heteroalkyl, optionally substituted $C_3$-$C_{10}$ cycloalkyl, or optionally substituted $C_3$-$C_{10}$ cycloheteroalkyl; and R' is optionally substituted $C_1$-$C_{10}$ alkyl, optionally substituted $C_3$-$C_{10}$ heteroalkyl, optionally substituted $C_3$-$C_{10}$ cycloalkyl, or optionally substituted $C_3$-$C_{10}$ cycloheteroalkyl.

In some embodiments of Formulae A1-A4, Q is:

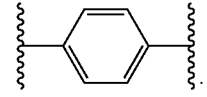

In some embodiments of Formulae A1-A4, Q is:

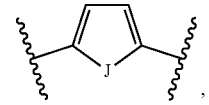

wherein J is i S, O, or $NR^8$; and $R^8$ is H, optionally substituted $C_1$-$C_{10}$ alkyl, optionally substituted $C_3$-$C_{10}$ heteroalkyl, optionally substituted $C_3$-$C_{10}$ cycloalkyl, optionally substituted $C_3$-$C_{10}$ cycloheteroalkyl, optionally substituted $C_6$-$C_{10}$ aryl, or optionally substituted $C_5$-$C_{10}$ heteroaryl.

In some embodiments of Formulae A1-A4, Q is:

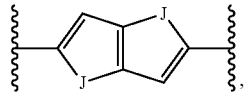

wherein J, at each occasion, is independently S, O, or $NR^8$; and $R^8$ is H, optionally substituted $C_1$-$C_{10}$ alkyl, optionally substituted $C_3$-$C_{10}$ heteroalkyl, optionally substituted $C_3$-$C_{10}$ cycloalkyl, optionally substituted $C_3$-$C_{10}$ cycloheteroalkyl, optionally substituted $C_6$-$C_{10}$ aryl, or optionally substituted $C_5$-$C_{10}$ heteroaryl.

In some embodiments, J is S. In some embodiments, J is O. In some embodiments, J is $NR^8$.

In some embodiments of Formulae A1-A4, A is:

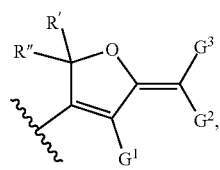

wherein R' and R" are independently selected from optionally substituted C1-C12 alkyl (e.g., fluorinated alkyl) and optionally substituted C6-C10 aryl (e.g., fluorinated aryl), and $G^1$, $G^2$, and $G^3$ are independently selected from electronegative groups that include F, CN, $CF_3$, $SO_2CF_3$.

In some embodiments, R' is $CF_3$. In other embodiments, R" is phenyl. In certain embodiments, $G^1$, $G^2$, and $G^3$ are CN.

In some embodiments, A is

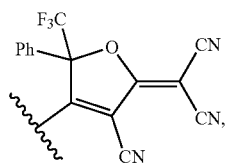 [SMILES: *C1=C(C#N)C(=C(C#N)C#N)OC1(c1ccccc1)C(F)(F)F]

In some embodiments, m is 1. In some embodiments, n is 1.

In some embodiments, the compound is a compound of Formula A5:

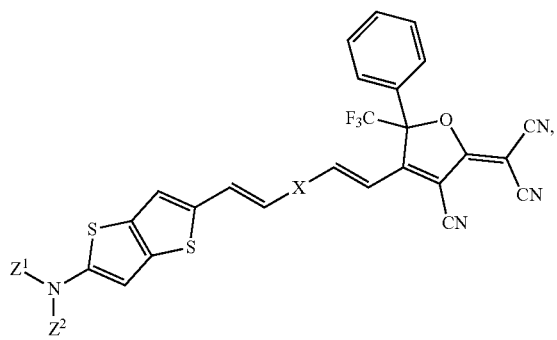

(A5)

wherein:

$Z^1$ and $Z^2$ are independently H, optionally substituted $C_1$-$C_{10}$ alkyl, optionally substituted $C_3$-$C_{10}$ heteroalkyl, optionally substituted $C_3$-$C_{10}$ cycloalkyl, optionally substituted $C_3$-$C_{10}$ cycloheteroalkyl, optionally substituted $C_6$-$C_{10}$ aryl, or optionally substituted $C_5$-$C_{10}$ heteroaryl;

X is:

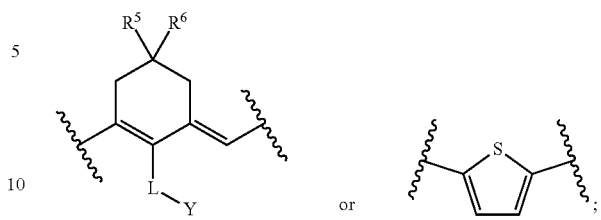

L is absent or L is S or O;

Y is H, optionally substituted $C_1$-$C_{20}$ alkyl, optionally substituted $C_3$-$C_{50}$ heteroalkyl, optionally substituted $C_3$-$C_{10}$ cycloalkyl, or optionally substituted $C_3$-$C_{10}$ cycloheteroalkyl; and $R^5$ and $R^6$ are independently H, optionally substituted $C_1$-$C_{10}$ alkyl, optionally substituted $C_3$-$C_{10}$ heteroalkyl, optionally substituted $C_3$-$C_{10}$ cycloalkyl, or optionally substituted $C_3$-$C_{10}$ cycloheteroalkyl.

In some embodiments, the compound is a compound of Formula A6:

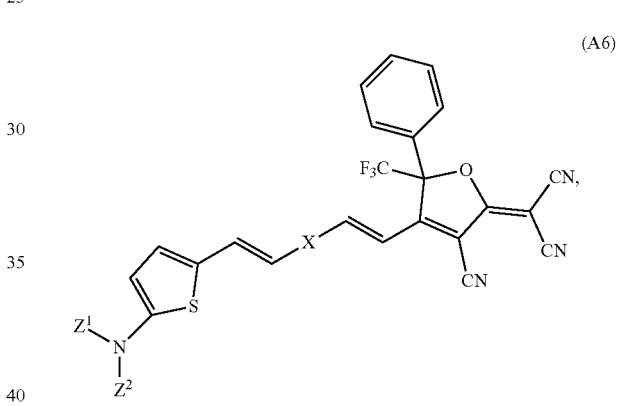

(A6)

wherein:

$Z^1$ is optionally substituted $C_6$-$C_{10}$ aryl or optionally substituted $C_5$-$C_{10}$ heteroaryl;

$Z^2$ is H, optionally substituted $C_1$-$C_{10}$ alkyl, optionally substituted $C_3$-$C_{10}$ heteroalkyl, optionally substituted $C_3$-$C_{10}$ cycloalkyl, optionally substituted $C_3$-$C_{10}$ cycloheteroalkyl, optionally substituted $C_6$-$C_{10}$ aryl, or optionally substituted $C_5$-$C_{10}$ heteroaryl;

X is:

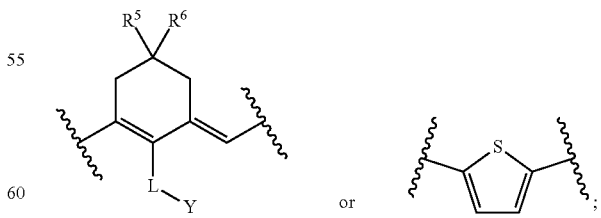

L is absent or L is S or O;

Y is H, optionally substituted $C_1$-$C_{20}$ alkyl, optionally substituted $C_3$-$C_{50}$ heteroalkyl, optionally substituted $C_3$-$C_{10}$ cycloalkyl, or optionally substituted $C_3$-$C_{10}$ cycloheteroalkyl; and $R^5$ and $R^6$ are independently H, optionally substituted $C_1$-$C_{10}$ alkyl, optionally substituted $C_3$-$C_{10}$ heteroalkyl, optionally substituted $C_3$-$C_{10}$ cycloalkyl, or optionally substituted $C_3$-$C_{10}$ cycloheteroalkyl.

In some embodiments, the compound is a compound of Formula A7:

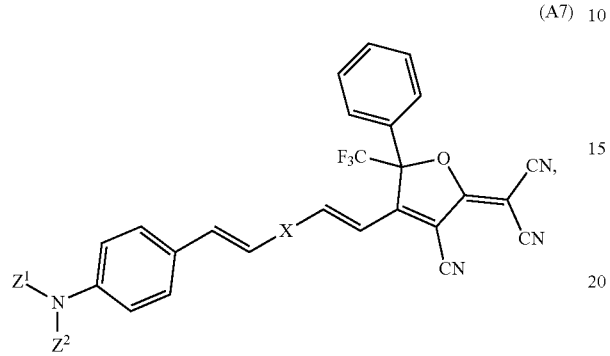

(A7)

wherein:

$Z^1$ is optionally substituted $C_6$-$C_{10}$ aryl or optionally substituted $C_5$-$C_{10}$ heteroaryl;

$Z^2$ is H, optionally substituted $C_1$-$C_{10}$ alkyl, optionally substituted $C_3$-$C_{10}$ heteroalkyl, optionally substituted $C_3$-$C_{10}$ cycloalkyl, optionally substituted $C_3$-$C_{10}$ cycloheteroalkyl, optionally substituted $C_6$-$C_{10}$ aryl, or optionally substituted $C_5$-$C_{10}$ heteroaryl;

X is:

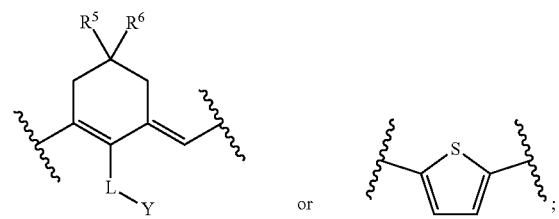

L is absent or L is S or O;

Y is H, optionally substituted $C_1$-$C_{20}$ alkyl, optionally substituted $C_3$-$C_{50}$ heteroalkyl, optionally substituted $C_3$-$C_{10}$ cycloalkyl, or optionally substituted $C_3$-$C_{10}$ cycloheteroalkyl; and $R^5$ and $R^6$ are independently H, optionally substituted $C_1$-$C_{10}$ alkyl, optionally substituted $C_3$-$C_{10}$ heteroalkyl, optionally substituted $C_3$-$C_{10}$ cycloalkyl, or optionally substituted $C_3$-$C_{10}$ cycloheteroalkyl.

The polarizable chromophores disclosed herein can comprise one or more reactive groups that can form a covalent bond (i.e., crosslink) when reacted with a counterpart group, for example, when subjected to high temperatures. Any suitable reactive groups and counterpart groups can be used to form the films comprising chromophores of the disclosure. In some embodiments, the reactive groups and counterpart groups are groups crosslinkable by (4+2) cycloaddition. A number of such groups is known in the art.

In some embodiments, one or more of Y, X, $R^1$, $R^2$, $R^3$, $R^4$, $R^5$, and $R^6$ comprise a reactive group. In some embodiments, one or more of Y, X, $R^1$, $R^2$, $R^3$, $R^4$, $R^5$, and $R^6$ are optionally substituted with one or more reactive group, for example, a group crosslinkable by (4+2) cycloaddition such as an anthracenyl group or an acrylate group. In some embodiments, the group crosslinkable by (4+2) cycloaddition is represented by the structure:

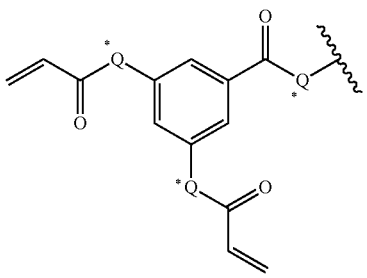

or

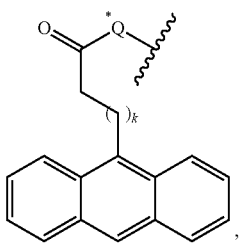

, wherein k is 0, 1, 2, 3, 4, or 5, and each Q* is independently NH, N(C1-C10-alkyl), O, or S.

In some embodiments, one or more of Y, X, $R^1$, $R^2$, $R^3$, $R^4$, $R^5$, and $R^6$ are optionally substituted with one or more functional groups or protected functional groups, which can be present in addition to the one or more reactive groups described above. As used herein, a "functional group" is a group, a substituent, or moiety responsible for the characteristic chemical reactions of the molecule that comprises such functional group. For example, a hydroxyl functional group is a group that can undergo esterification reaction; a hydroxyl functional group can be protected with a silyl protective group, such as trimethylsilyl or tert-butyldiphenylsilyl (TBDPS).

In some embodiments of the Formulae of the disclosure, L-Y is H, $OL^1OSiR^{10}R^{11}R^{12}$, or $SL^1OSiR^{10}R^{11}R^{12}$, wherein $L^1$ is an optionally substituted $C_2$-$C_{20}$ alkylene or optionally substituted $C_3$-$C_{50}$ heteroalkylene; and $R^{10}$, $R^{11}$, and $R^{12}$ are independently H, C1-C10 alkyl, or C6-C10 aryl. In some embodiments, L-Y is H. In some embodiments, L-Y is —$SCH_2CH_2OH$ or $SCH_2CH_2OTBDPS$.

In some embodiments, $R^1$ is methyl or optionally substituted ethyl. In some embodiments, $R^2$ is methyl or optionally substituted ethyl. In some embodiments, $R^3$ is methyl or optionally substituted ethyl. In some embodiments, $R^4$ is methyl or optionally substituted ethyl.

In some embodiments, $R^5$ is $CH_3$ and $R^6$ is $CH_3$.

In some embodiments of the compounds disclosed herein, at least one of $Z^1$ and X is substituted with a group selected from

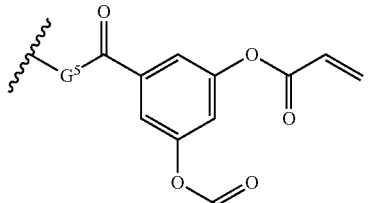

,

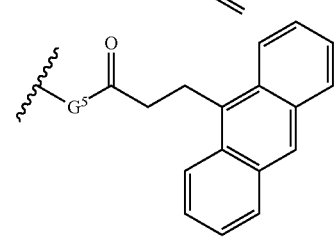

, and $OSiR^{10}R^{11}R^{12}$,
wherein $G^5$ is NH, O, S, or N(C1-C10-alkyl) and $R^{10}$, $R^{11}$, and $R^{12}$ are independently H, optionally substituted C1-C10 alkyl, or optionally substituted C6-C10 aryl.

In some embodiments of the compounds disclosed herein, L-Y is H, $OL^1OSiR^{10}OR^{11}R^{12}$, or $SL^1OSiR^{10}R^{11}R^{12}$, wherein $L^1$ is an optionally substituted C2-C20 alkylene or optionally substituted C3-C50 heteroalkylene; and $R^{10}$, $R^{11}$, and $R^{12}$ are independently H, optionally substituted C1-C10 alkyl, or optionally substituted C6-C10 aryl.

In some embodiments of the compounds disclosed herein, X is:

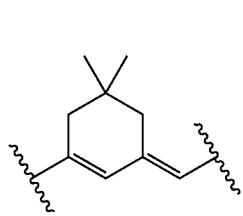 or 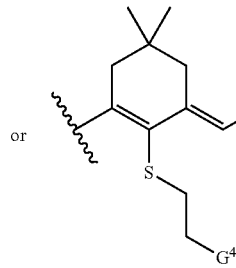, wherein $G^4$ is $OSiR^{10}R^{11}R^{12}$, wherein $R^{10}$, $R^{11}$, and $R^{12}$ are independently H, optionally substituted C1-C10 alkyl, or optionally substituted C6-C10 aryl, or $G^4$ is

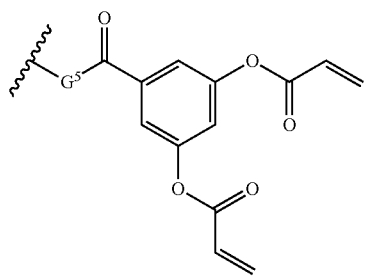

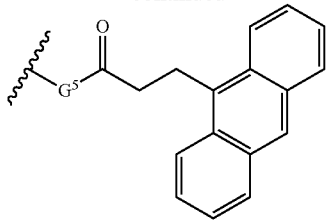

, wherein $G^5$ is NH, O, S, or N(C1-C10-alkyl).

In some embodiments, X is:

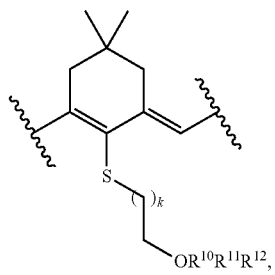

wherein k is an integer from 1 to 20 and $R^{10}$, $R_{11}$, and $R^{12}$ are independently H, C1-C10 alkyl, or C6-C10 aryl.

In some embodiments, X is:

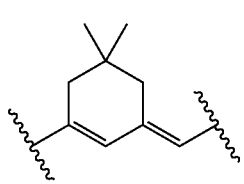 or 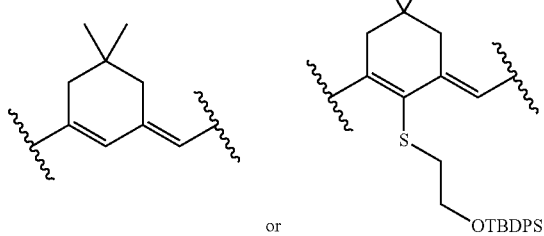

wherein TBDPS is

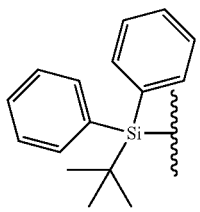

.

In some embodiments, the compound is a compound of Formula A8:

(A8)

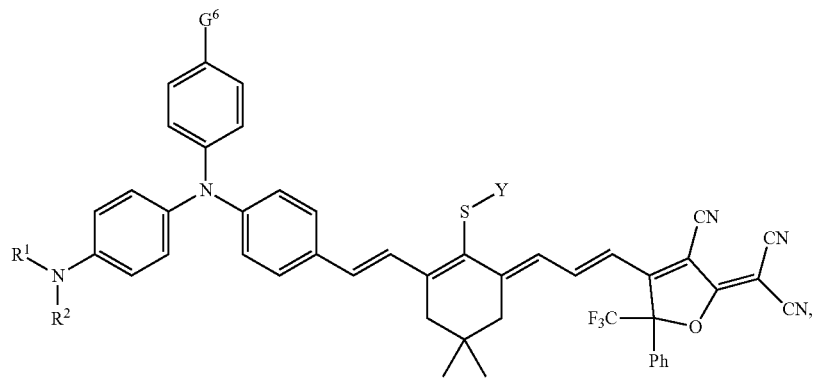

wherein:

$G^6$ is OR' or NR'R", wherein R' and R" are independently optionally substituted C1-C10 alkyl;

$R^1$ is H or an optionally substituted C1-C10 alkyl, $R^2$ is optionally substituted $C_1$-$C_{10}$ alkyl, optionally substituted $C_3$-$C_{10}$ heteroalkyl, optionally substituted $C_3$-$C_{10}$ cycloalkyl, or optionally substituted $C_3$-$C_{10}$ cycloheteroalkyl; and Y is optionally substituted $C_1$-$C_{10}$ alkyl, optionally substituted $C_3$-$C_{10}$ heteroalkyl, optionally substituted $C_3$-$C_{10}$ cycloalkyl, or optionally substituted $C_3$-$C_{10}$ cycloheteroalkyl; and wherein at least one of $R^2$, Y, and $G^6$ is substituted with a group selected from

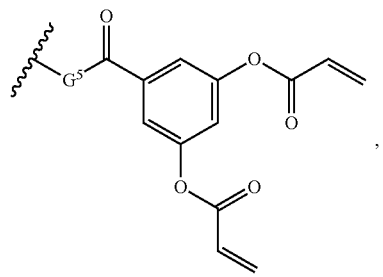

,

-continued

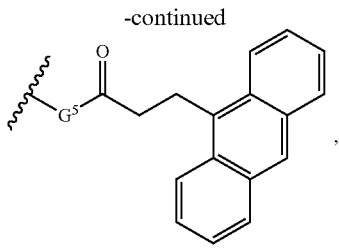

, and $OSiR^{10}R^{11}R^{12}$, wherein $G^5$ is NH, O, S, or N(C1-C10-alkyl) and $R^{10}$, $R^{11}$, and $R^{12}$ are independently H, optionally substituted C1-C10 alkyl, or optionally substituted C6-C10 aryl.

In some embodiments, the compound is Compound I, Compound II, Compound III, or Compound IV, Compound V, Compound VI, Compound VII, Compound VIII, Compound IX, Compound X, Compound XI, Compound XII, Compound XIII, Compound XIV, or Compound XV:

(I)

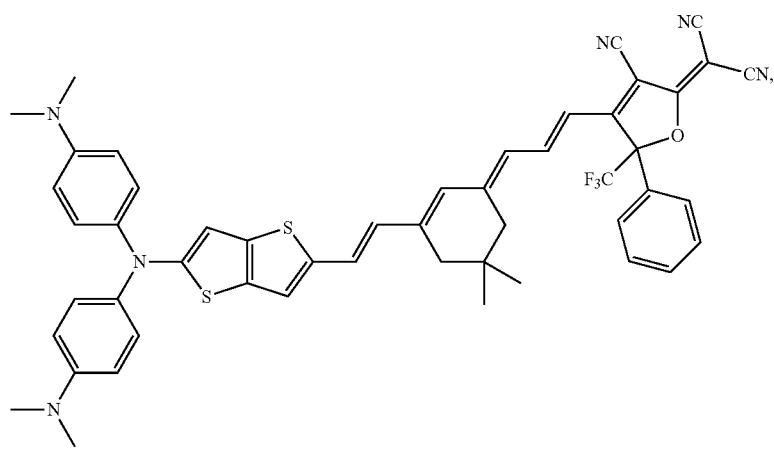

-continued
(II)
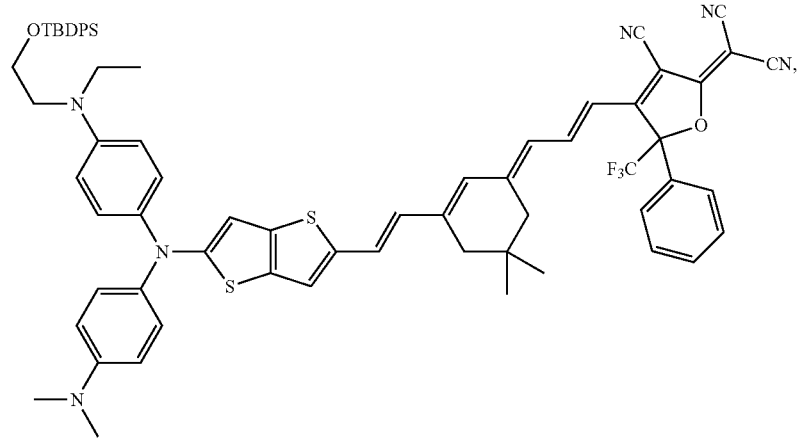
(III)
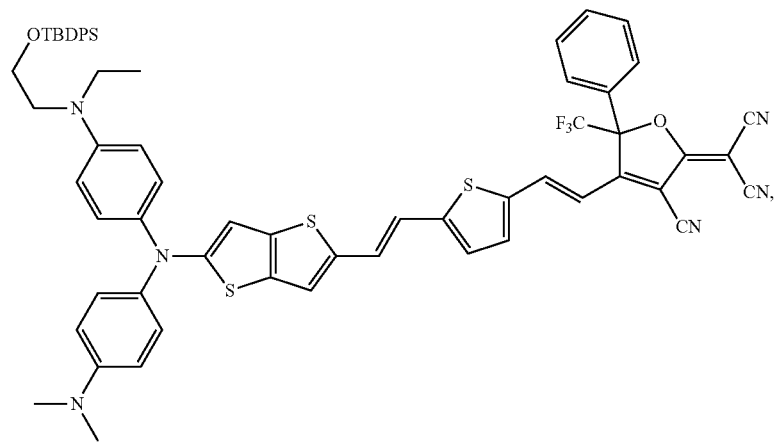
(IV)
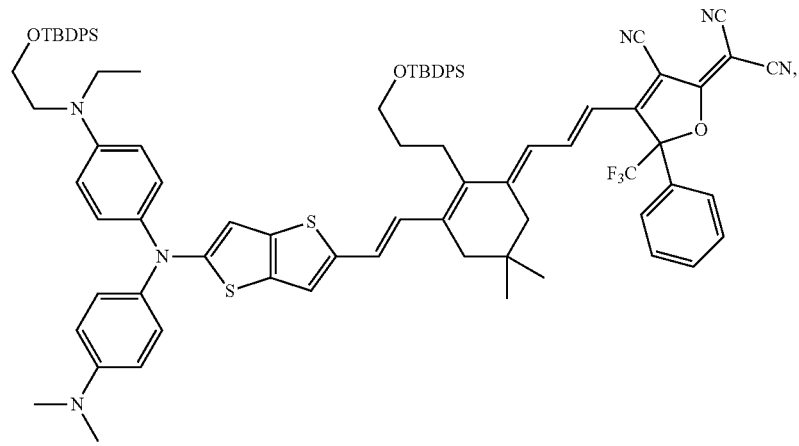

-continued
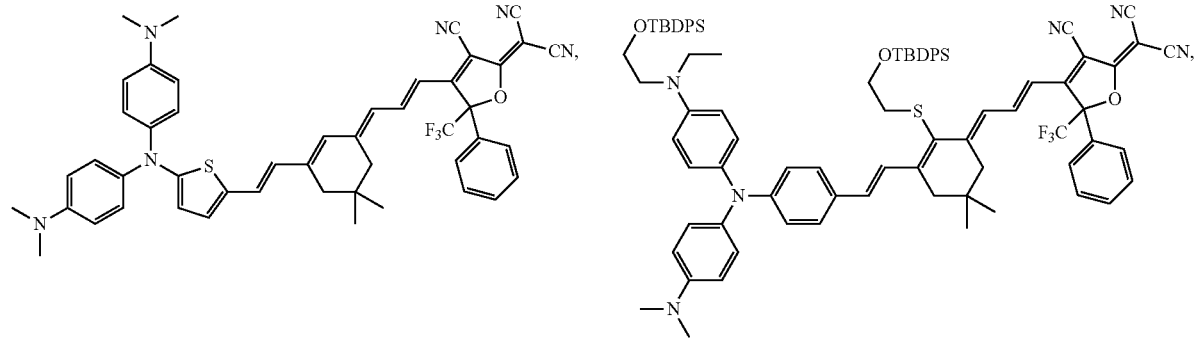
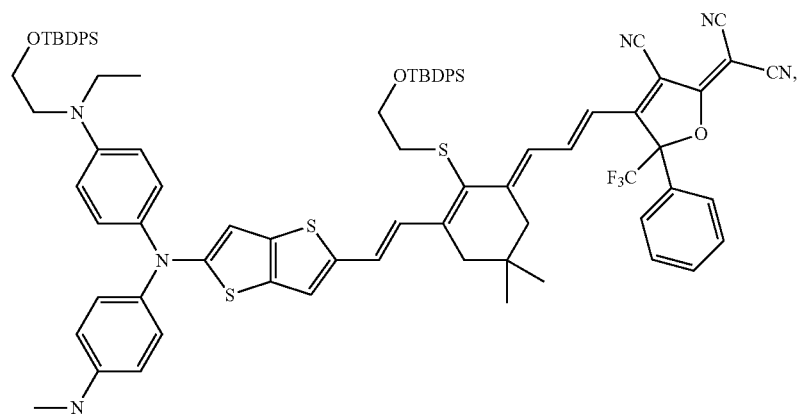
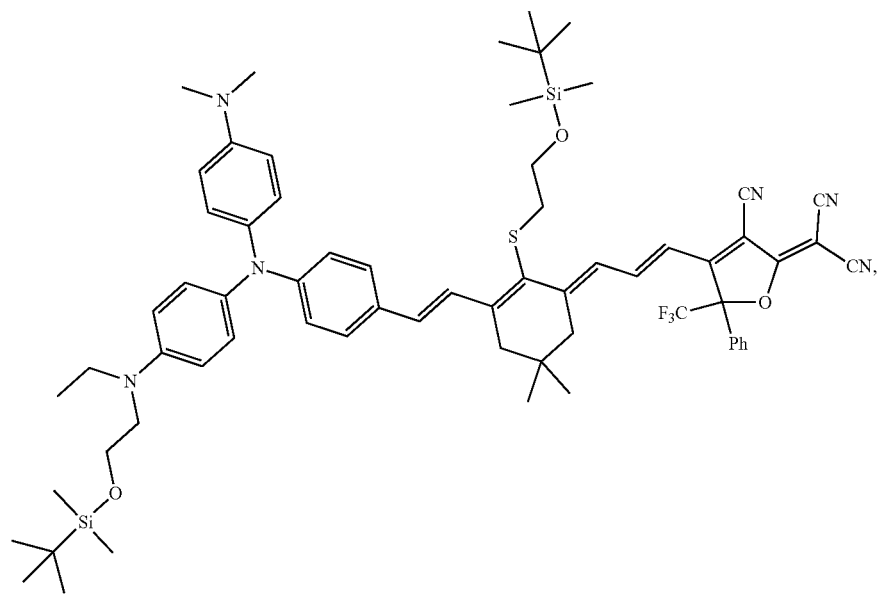

(IX)
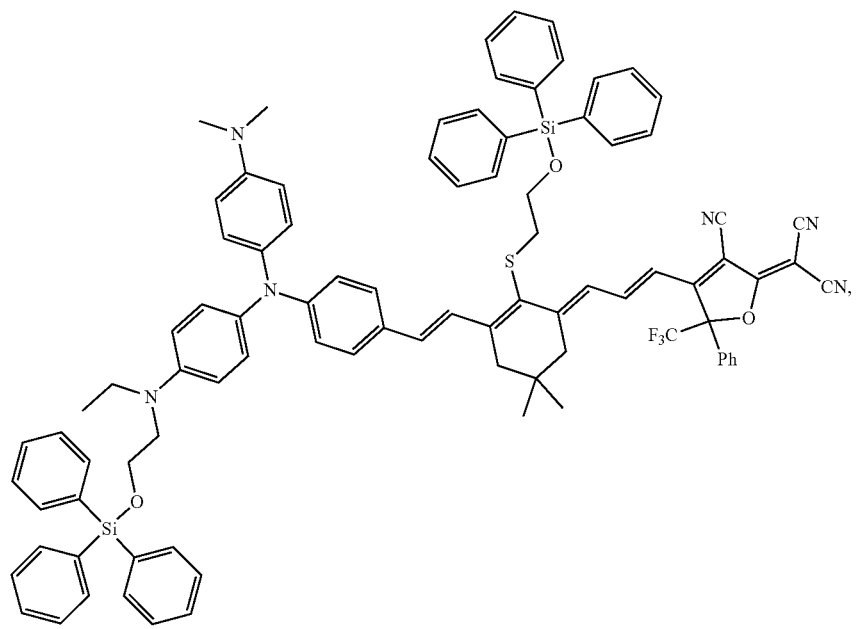
(X)
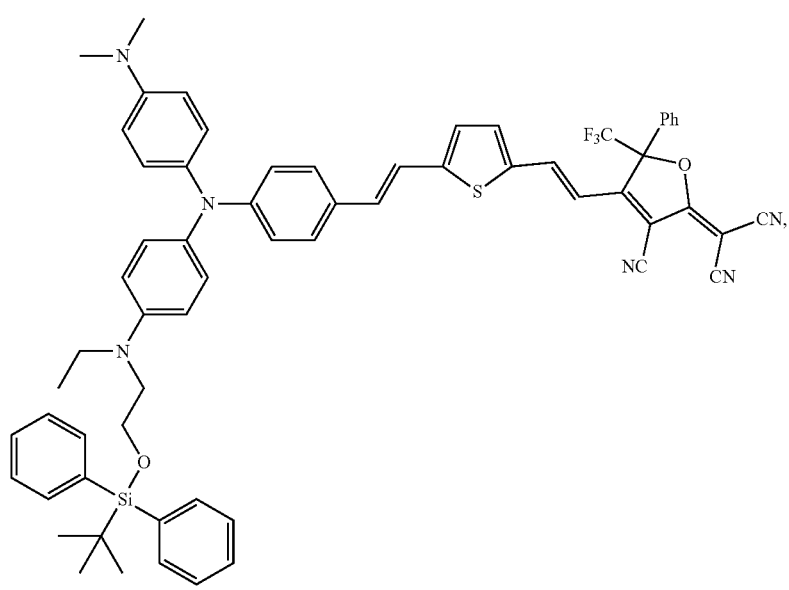

(XI)
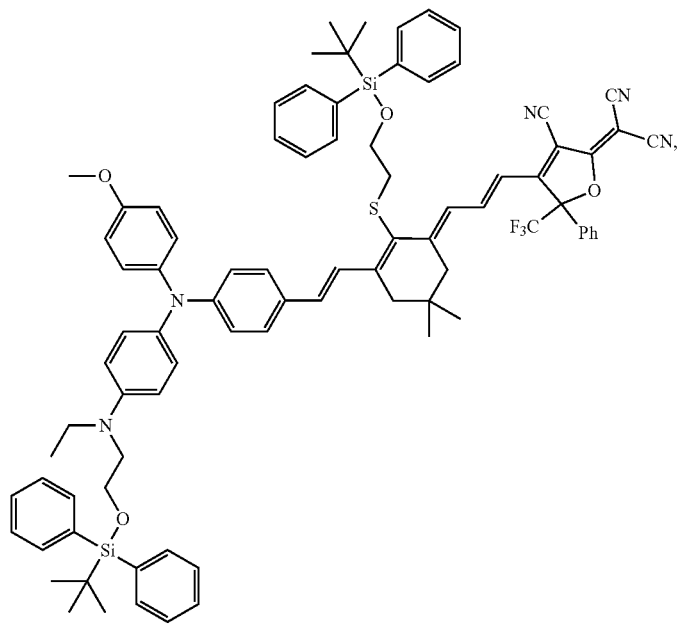
(XII)
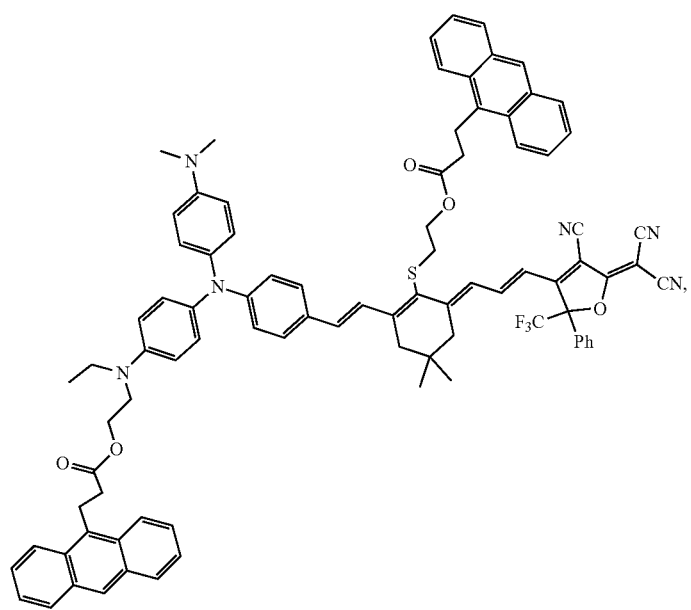

(XIII)

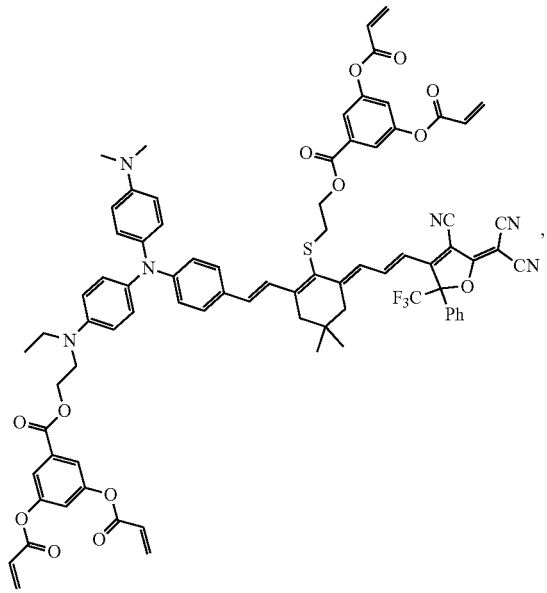

(XIV)

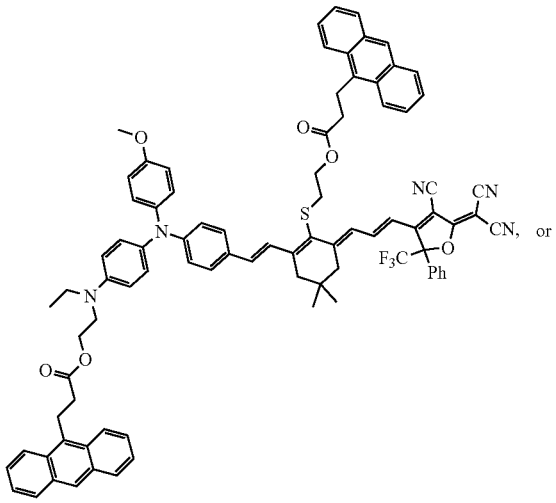

, or (XV)

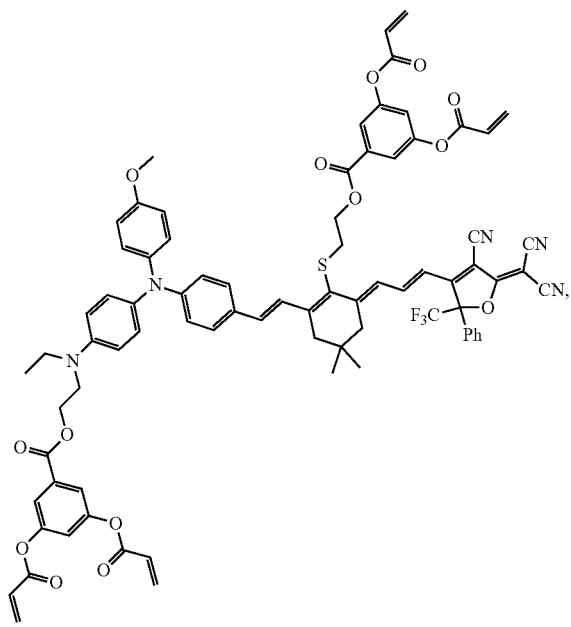

, wherein TBDPS is

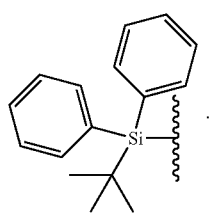 [SMILES: *[Si](c1ccccc1)(c1ccccc1)C(C)(C)C]

Figure 2:
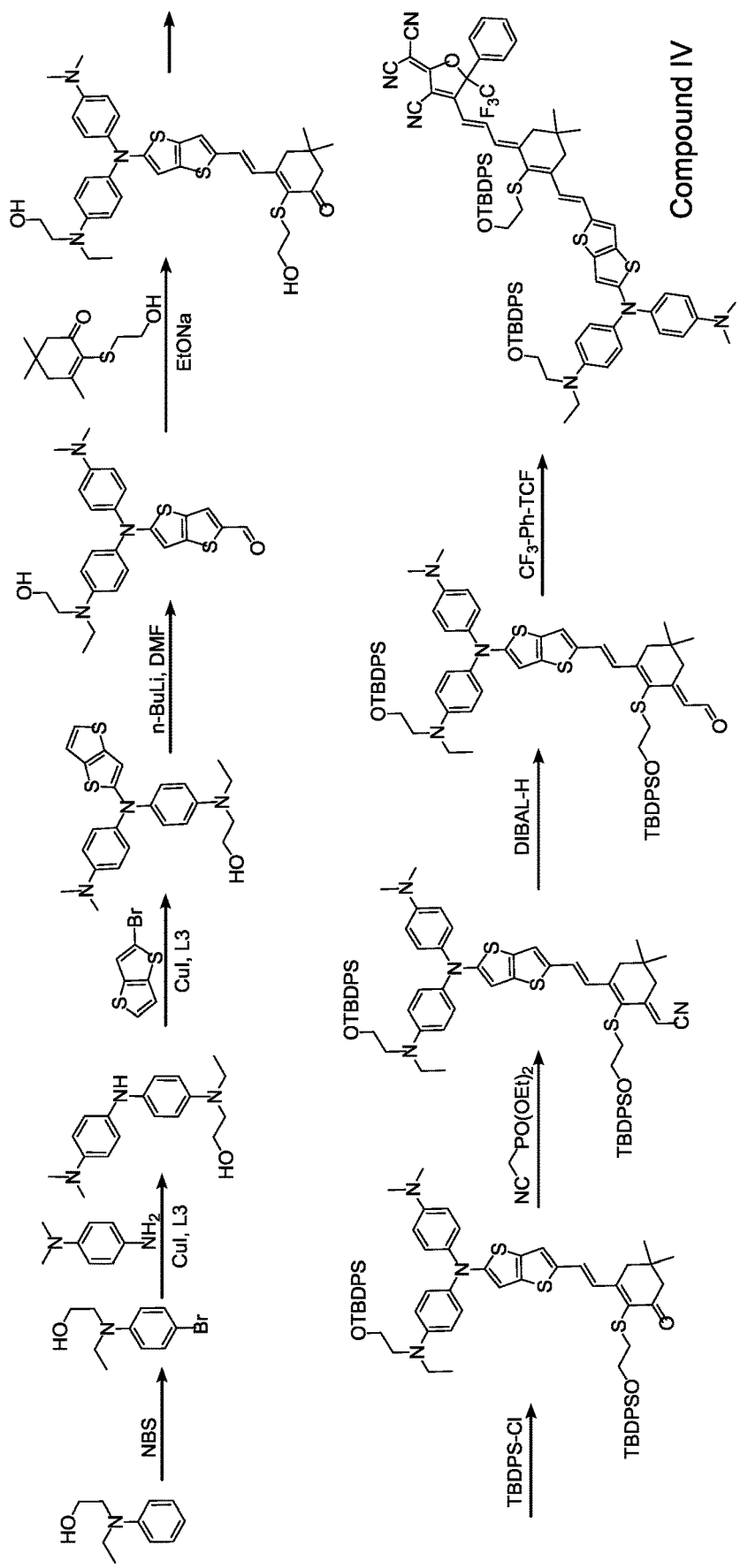
FIG. 2 shows the synthesis of an exemplary chromophore Compound IV.
Figure 7:
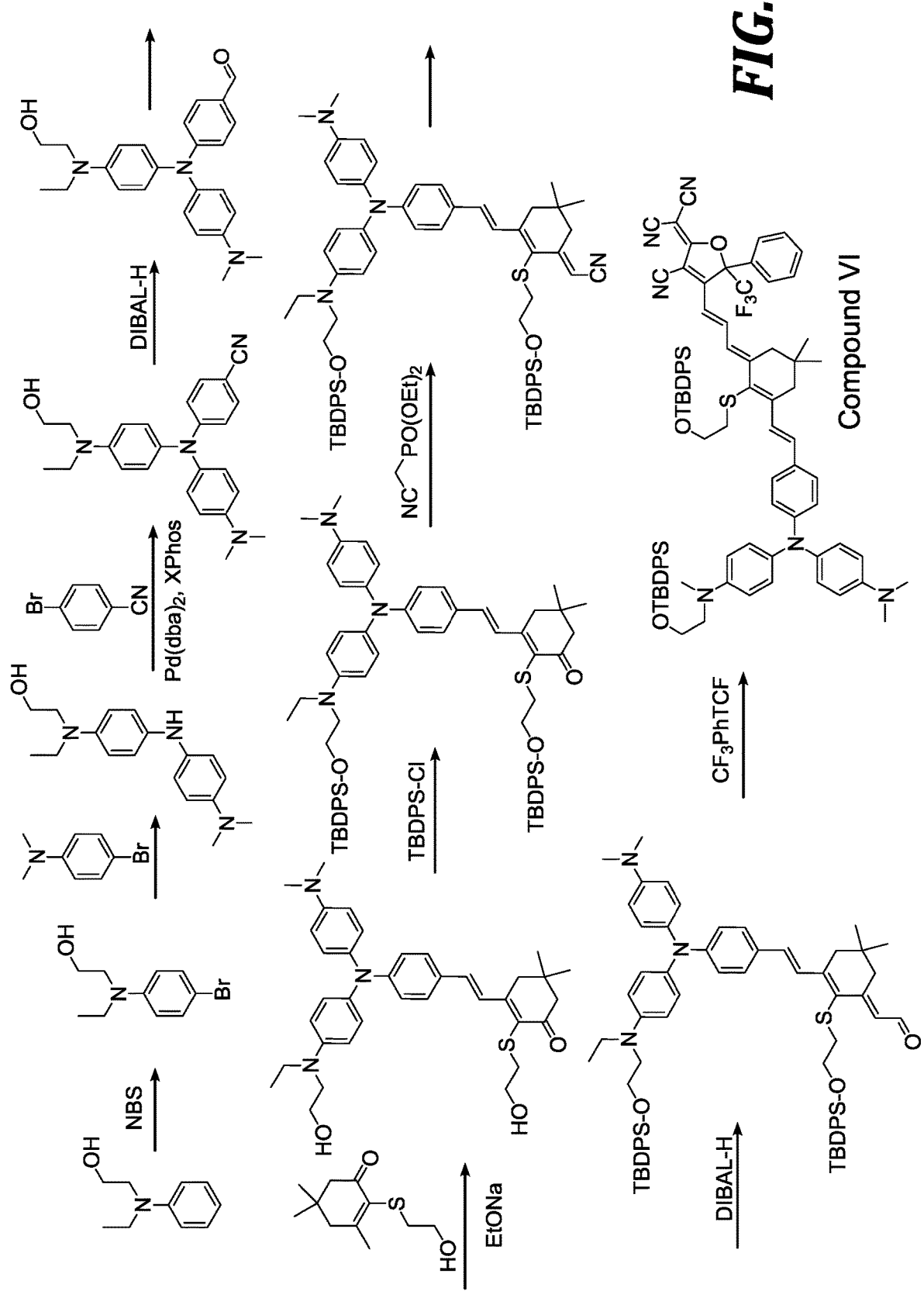
FIG. 7 shows the synthesis of an exemplary chromophore Compound VI.

The chromophores disclosed herein, such as compounds of Formulae A, A1, A2, A3, A4, A5, A6, A7, A8, I, II, III, IV, V, VI, VII, VIII, IX, XI, XII, XIII, XIV, and XV can be made using standard organic synthetic methods known to those skilled in the art using the intermediates common to a number known OEO chromophores, including substituted thioether-substituted isophorones and the $CF_3$-phenyl substituted tricyanofuran (TCF) acceptor, such as those described in Dalton, L. R.; Sullivan, P. A.; Bale, D. H., Electric Field Poled Organic Electro-optic Materials: State of the Art and Future Prospects. *Chemical Reviews* 2010, 110 (1), 25-55, the disclosure of which is incorporated herein by reference in its entirety. Synthesis of exemplary chromophores is shown in FIG. 2 and FIG. 7.

In some embodiments, the chromophores disclosed herein have a large static hyperpolarizability. In certain embodiments, the chromophores disclosed herein have a static hyperpolarizability between about one and a half times to about three times that of a reference chromophore JRD1

(FIG. 1), for example, as measured by Hyper-Rayleigh Scattering at 1300 nm in chloroform solution and extrapolated to zero frequency using a damped two-level model. In some embodiments, the chromophores disclosed herein have a static hyperpolarizability in excess of between about one and a half times to about three times that of a reference chromophore JRD1.

In another aspect, provided herein are polymeric compositions comprising the chromophores disclosed herein. In certain embodiments, the chromophores are blended with a polymer to form a processible and durable film that can have electro-optic activity induced by electric field poling, a process in which a strong, direct-current electric field is applied to the film, the film is heated to near its glass transition temperature ($T_g$) to enable chromophores to re-orient such that their dipole moments have net alignment with the field, and then cooled while still in the presence of the field to retain the poling-induced order. Electro-optic activity can be measured by Teng-Man ellipsometry, attenuated total reflection (ATR), methods known to those skilled in the art.

In certain embodiments, films containing the chromophores disclosed herein blended with polymethylmethacrylate (PMMA) have a $r_{33}$ value from about 70 pm/V to about 300 pm/V, from about 40 pm/V to about 140 pm/V, from about 30 pm/V to about 250 pm/V, from about 75 pm/V to about 300 pm/V, from about 80 pm/V to about 250 pm/V, from about 50 pm/V to 200 pm/V, from about 15 to about 105 pm/V, from about 105 to about 405 pm/V, from about 125 to about 1100 pm/V, from about 125 to about 1200 pm/V, from about 125 to about 1300 pm/V, from about 125 to about 1500 pm/V, in excess of about 350 pm/V, in excess of about 500 pm/V, in excess of about 750 pm/V, or in excess of about 1000 pm/V, as measured by Teng-Man ellipsometry.

In some embodiments, the films comprising the chromophores described herein can be combined with films of a dielectric material or wide-bandgap semiconductor as a charge blocking layer, for example, in order to minimize conductivity during poling of the film. Such films can comprise organic materials such as poly(benzocyclobutene) (BCB, Cyclotene™) or inorganic materials, including but not limited to, $TiO_2$, $MoO_3$, $ZrO_2$, $HfO_2$, $SiO_2$, $Al_2O_3$, $Si_3N_4$, or combinations thereof. In some embodiments, the films comprise poly(benzocyclobutene). In some embodiments, the BCB layer has a thickness from about 40 nm to about 150 nm or from about 60 nm to about 100 nm. In some embodiments, the charge blocking layer are such as the layers described in "Benzocyclobutene barrier layer for suppressing conductance in nonlinear optical devices during electric field poling" *Applied Physics Letters* 104, 243304 (2014).

In yet another aspect, provided herein are electro-optic devices comprising the films disclosed herein or films formed by the methods disclosed herein. Exemplary devices incorporating the films of the disclosure include an electro-optic modulator, antenna, Mach-Zehnder modulator, phase modulator, silicon-organic hybrid modulator, plasmonic-organic hybrid modulator, electrical-to-optical convertor, terahertz detector, frequency shifter, or frequency comb source. In some embodiments, the electro-optic devices comprising the films disclosed herein further comprise one or more charge blocking layers as described above.

Certain components of optical communications systems can be fabricated, in whole or part, with the films according to the present disclosure. Exemplary components include, without limitation, straight waveguides, bends, single-mode splitters, couplers (including directional couplers, MMI couplers, star couplers), routers, filters (including wavelength filters), switches, modulators (optical and electro-optical, e.g., birefringent modulator, the Mach-Zehnder interferometer, and directional and evanescent coupler), arrays (including long, high-density waveguide arrays), optical interconnects, optochips, single-mode DWDM components, photonic crystal devices, resonant devices (e.g., photonic crystal, ring, or disc resonators, and gratings. The films described herein may be used with, for example, wafer-level processing, as applied in, for example, vertical cavity surface emitting laser (VCSEL) and CMOS technologies.

In many applications, the films described herein can be used in lieu of lithium niobate, gallium arsenide, and other inorganic materials that currently find use as light-transmissive materials in optical communication systems.

Unless specifically defined herein, all terms used herein have the same meaning as they would to one skilled in the art of the present invention.

As used herein, the term "about" indicates that the subject value can be modified by plus or minus 5% and still fall within the disclosed embodiment.

The use of the term "or" in the claims is used to mean "and/or" unless explicitly indicated to refer to alternatives only or the alternatives are mutually exclusive, although the disclosure supports a definition that refers to only alternatives and "and/or." The words "a" and "an," when used in conjunction with the word "comprising" in the claims or specification, denote one or more, unless specifically noted.

Unless the context clearly requires otherwise, throughout the description and the claims, the words "comprise," "comprising," and the like, are to be construed in an inclusive sense as opposed to an exclusive or exhaustive sense; that is to indicate, in the sense of "including, but not limited to." Words using the singular or plural number also include the plural and singular number, respectively. For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element. Additionally, the words "herein," "above," and "below," and words of similar import, when used in this application, shall refer to this application as a whole and not to any particular portions of the application.

All publications cited herein and the subject matter for which they are cited are hereby specifically incorporated by reference in their entireties.

The following examples are provided to illustrate certain particular features and/or embodiments of the disclosure. The examples should not be construed to limit the disclosure to the particular features or embodiments described.

EXAMPLES

Using density functional theory (DFT) calculations performed using well-validated methods, the inventors found that the chromophores of the disclosure, such as Compounds I and II, can have large hyperpolarizability. Calculations were performed at the M062X/6-31+G(d) level of theory in a chloroform implicit solvent environment (PCM), with hyperpolarizabilities calculated using analytic differentiation (CPHF). Identical calculations were also performed on a truncated model of JRD1 as a standard; the OTBDPS groups on the donor in JRD1 were replaced with hydrogens for computational efficiency, modeling the donor as a diethylaniline. Computed hyperpolarizabities were reported in reference to this model. Exemplary Compounds I-XV were synthesized using standard organic synthesis methods known to those skilled in the art, and composition was verified by proton ($^1$H) NMR and electrospray ionization mass spectrometry (ESI-MS). UV/Visible absorbance spectra were measured in both chloroform and thin films using methods known to those skilled in the art.

Hyperpolarizabilities of exemplary Compounds I, II, III, IV, V, VI, and VII in chloroform solution were determined by hyper-Rayleigh scattering (HRS) with light produced by a high-repetition rate (80 MHz) broadband (680-1300 nm) femtosecond-pulsed laser (Insight DS+, Spectra-Physics) tuned to 1300 nm, as previously described (Campo, J.; Desmet, F.; Wenseleers, W.; Goovaerts, E., Highly sensitive setup for tunable wavelength hyper-Rayleigh scattering with parallel detection and calibration data for various solvents. *Optics Express* 2009, 17 (6), the disclosure of which is incorporated herein by reference). Measurements were performed relative to a pure chloroform standard, and data was extrapolated to zero frequency using the damped two-level model and a linewidth of 0.1 eV. In order to provide a clearer comparison to the state of the art and remove dependence on the reference value used for chloroform, state-of-the-art chromophore JRD1 was measured in the same experiment set and data is also reported relative to JRD1. Data from DFT, UV/Vis, and HRS measurements are summarized in Table 1.

TABLE 1

Key optical properties for exemplary chromophores

| Compound | $\lambda_{max}$ in CHCl$_3$ (nm) | $\lambda_{max}$ in neat film (nm) | $\beta_0/\beta_{0,JRD1}$ (DFT) | $\beta_0/\beta_{0,JRD1}$ (HRS) |
|---|---|---|---|---|
| JRD1 | 784 | 900 | 1 (ref) | 1 (ref) |
| I | 1058 | 1105 | 2.16 | 2.85 ± 0.10 |
| II | 1068 | 1103 | 2.19 | 2.60 ± 0.04 |
| III | 943 | 951 | 1.85 | 2.47 ± 0.04 |
| IV | 1081 | 1114 | 2.32 | 3.34 ± 0.04 |
| V | 1028 | — | 1.76 | 1.18 ± 0.12 |
| VI | 897 | 935 | 1.52 | 2.15 ± 0.09 |
| VII | 1020 | 1097 | 1.76 | 2.83 ± 0.17 |

Exemplary thin films comprising exemplary Compounds I, II, III, IV, VI, and VII were formed on glass slides and/or glass slides on which half of the slide was coated with a conductive layer of indium tin oxide (ITO); ITO slides were fabricated by Thin Film Devices (Anaheim, Calif.). Chromophores were deposited by spin coating from trichloroethane (TCE) solutions containing the chromophore, either neat or blended with PMMA. Films were dried in a vacuum oven at 65° C. before use.

Figure 3A:
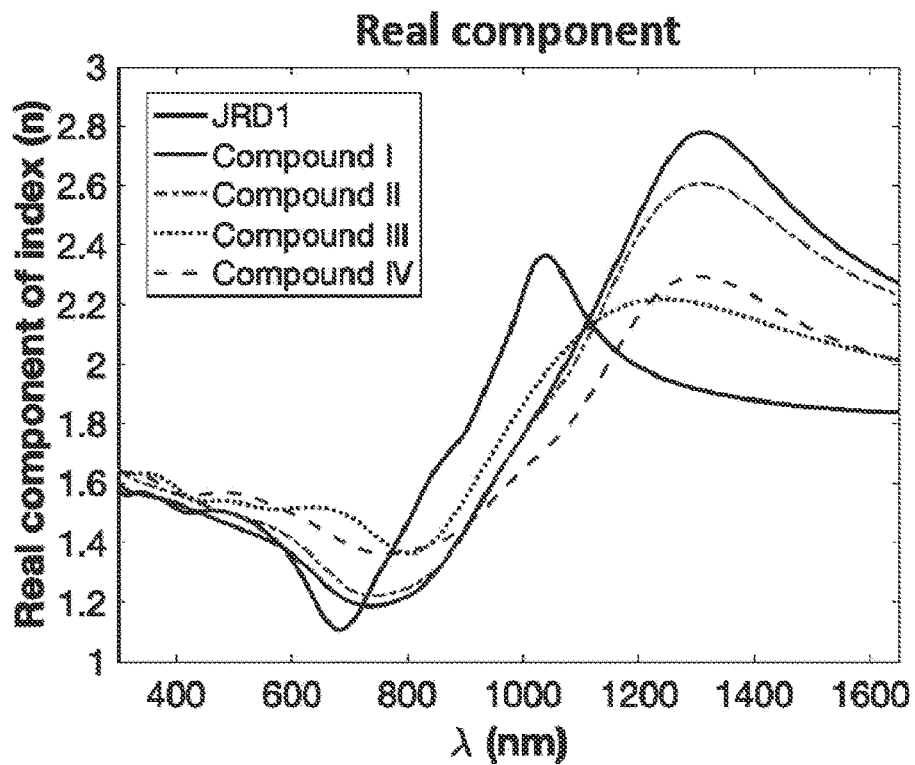
FIGS. 3A and 3B depicts real (n, FIG. 3A) and imaginary (k, FIG. 3B) (components of the refractive index for exemplary chromophores Compound I, Compound II, Compound III, or Compound IV.
Figure 3B:
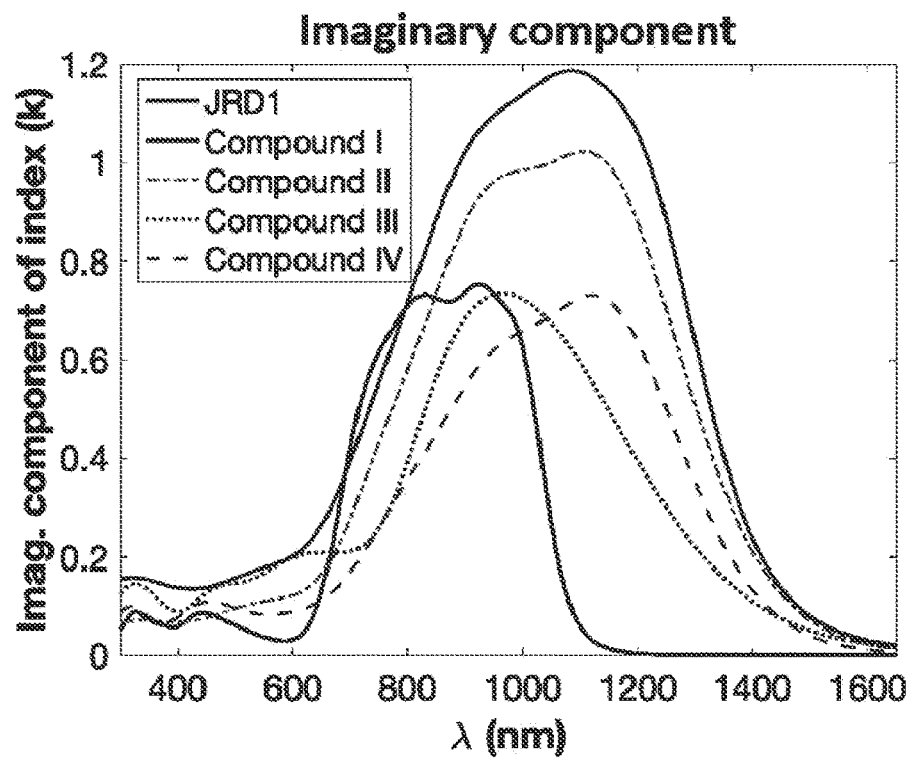
Figure 4A:
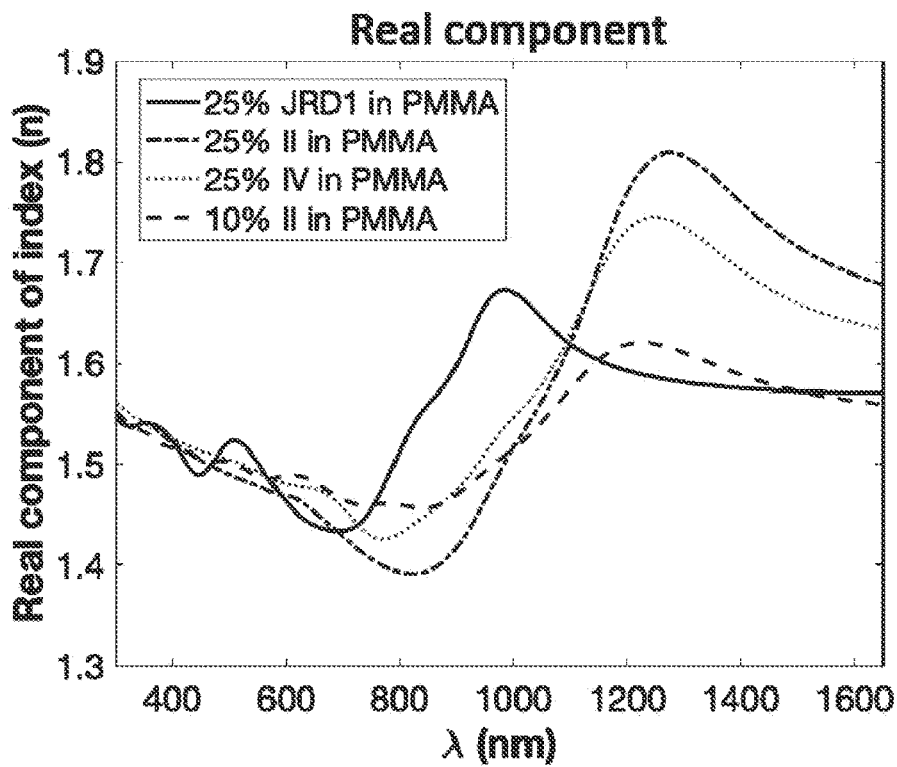
FIGS. 4A and 4B shows real (n, FIG. 4A) and imaginary (k, FIG. 4B) components of the refractive index for 10 wt % and 25 wt % concentrations of exemplary Compound II and 25 wt % concentration of exemplary Compound IV compared with 25 wt % JRD1 in PMMA.
Figure 4B:
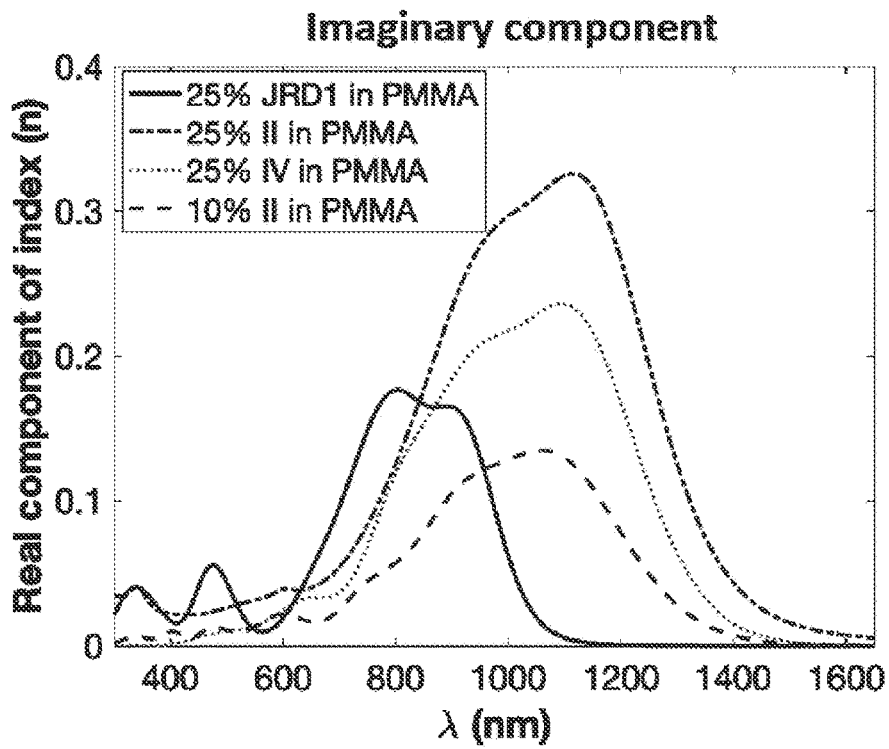
Figure 5A:
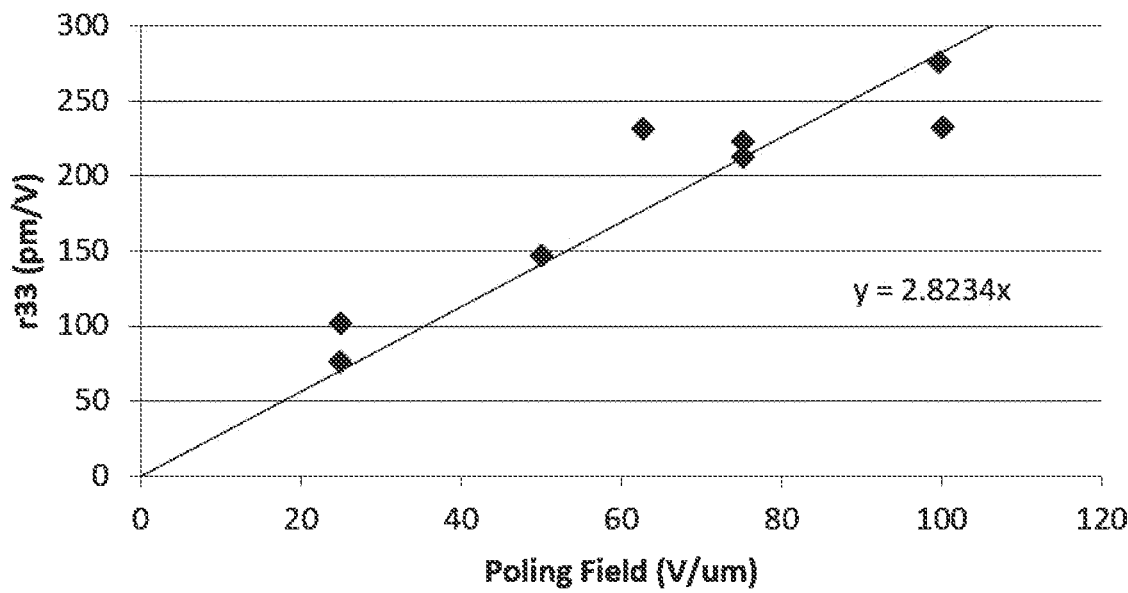
FIGS. 5A-5D show electro-optic measurements on thin films for exemplary Compound II (5A and 5B) and exemplary Compound IV (5C and 5D) in PMMA obtained at 1310 nm using the Teng-man ellipsometry method.
Figure 5B:
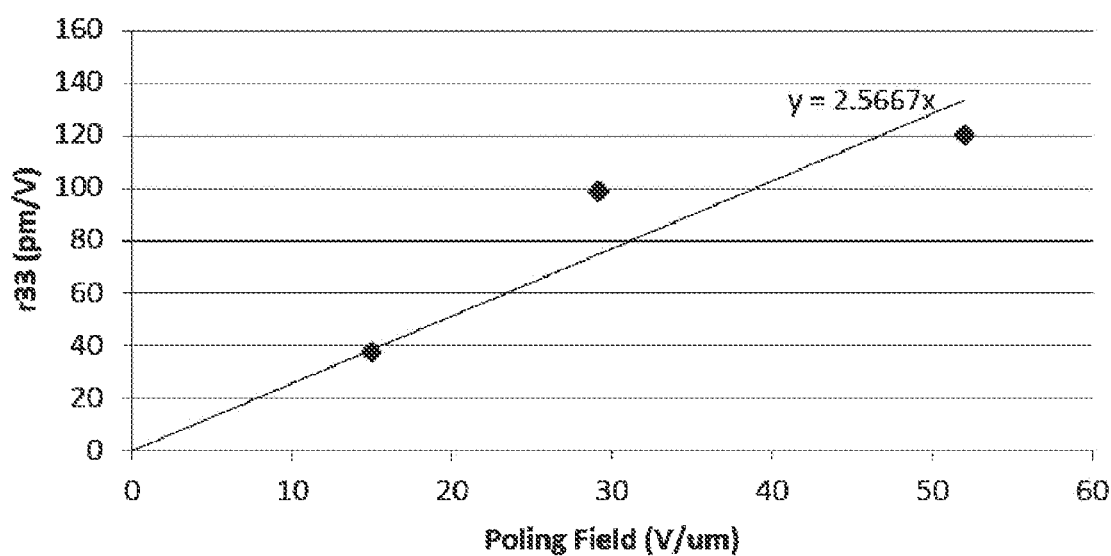
Figure 5C:
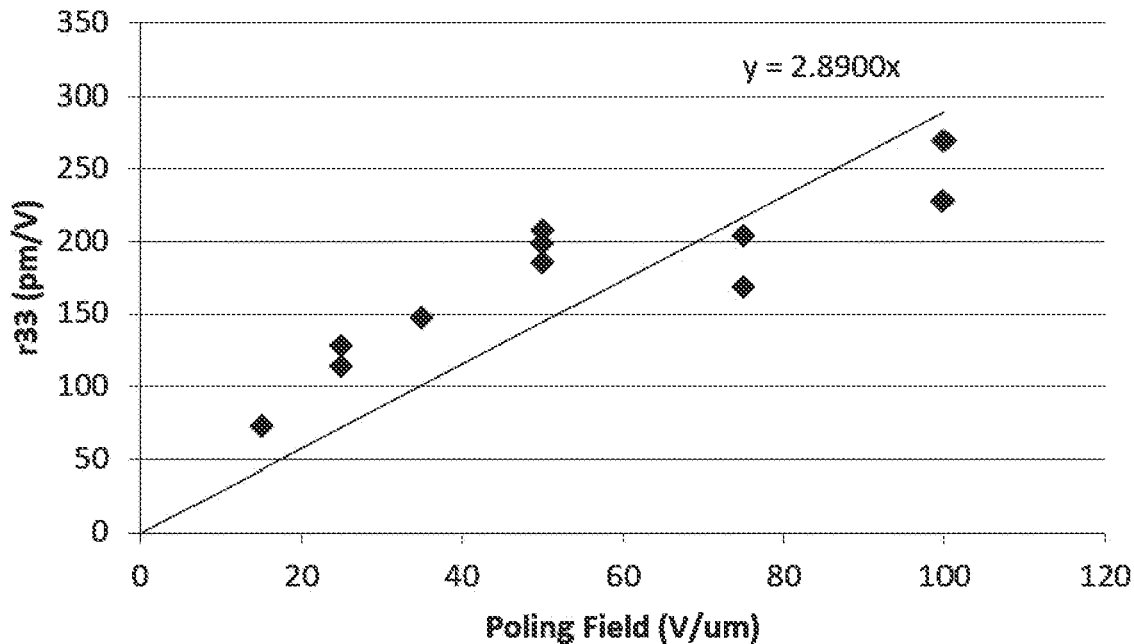
Figure 5D:
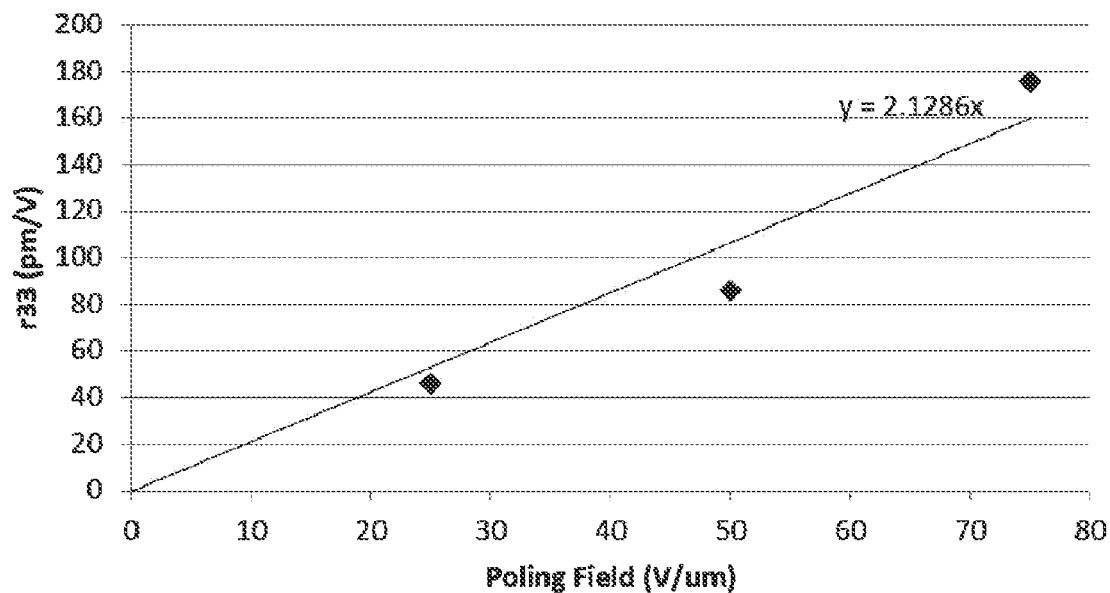

The complex refractive indices (n and k) of thin films comprising exemplary Compounds I, II, III, and IV on glass substrates were determined using Variable Angle Spectroscopic Ellipsometry (VASE) at the UW Molecular Analysis Facility using a JA Woollam MC2000 spectroscopic ellipsometer and previously reported methods (Benight, S. J.; Johnson, L. E.; Barnes, R.; Olbricht, B. C.; Bale, D. H.; Reid, P. J.; Eichinger, B. E.; Dalton, L. R.; Sullivan, P. A.; Robinson, B. H., Reduced Dimensionality in Organic Electro-Optic Materials: Theory and Defined Order. *The Journal of Physical Chemistry B* 2010, 114 (37), 11949-11956, the disclosure of which is incorporated herein by reference). Data for exemplary Compounds I, II, III, and IV as neat films is shown in FIG. 3. Data for films of Compound II in PMMA and compared with neat JRD1 is shown in FIG. 4. The data in FIG. 4 is representative for the behavior of the compounds disclosed herein when blended in dilute polymer films.

Films for electro-optic measurements were prepared by sputter-coating gold electrodes on thin films of exemplary Compounds I, II, III, IV, VI, and VII attaching wires using commercially available silver paste, poling at a temperature appropriate for the $T_g$ of the material (approximately 115° C. for blends in PMMA, 85-90° C. for neat materials) using a poling field of $E_p$ with a strength in the 15 V/μm to 110 V/μm range, cooling to <35° C. and measuring electro-optic activity at 1310 nm using previously reported methods and instrumentation (Dalton, L. R.; Sullivan, P. A.; Bale, D. H., Electric Field Poled Organic Electro-optic Materials: State of the Art and Future Prospects. *Chemical Reviews* 2010, 110 (1), 25-55, the disclosure of which is incorporated herein by reference). Representative poling results for exemplary Compounds II and III are shown in FIG. 5. Poling efficiencies $r_{33}/E_p$ were determined by linear fitting of the electro-optic activity (in pm/V) versus $E_p$.

In addition to the data shown in FIG. 5, exemplary Compound I at 10% concentration by mass in PMMA demonstrated a poling efficiency of 1.77 nm$^2$/V$^2$ and Compound III at 25% concentration by mass in PMMA demonstrated a poling efficiency of 2.87 nm$^2$/V$^2$. The poling efficiencies compare highly favorably to 25% JRD1 in PMMA (~1 nm$^2$/V$^2$). The poling efficiencies of exemplary Compounds II and IV at low concentrations are particularly extraordinary for their number density. Exemplary Compound II at 10% concentration in PMMA (2.82 nm$^2$/V$^2$) and exemplary Compound IV at 10% concentration in PMMA (2.86 nm$^2$/V$^2$) were competitive with neat JRD1, which has a poling efficiency of 3.43±0.2 nm$^2$/V$^2$ with a BCB charge blocking layer between the ITO and OEO material and 3.1±0.1 without a charge blocking layer, as disclosed in Jin, W.; Johnston, P. V.; Elder, D. L.; Tillack, A. F.; Olbricht, B. C.; Song, J.; Reid, P. J.; Xu, R.; Robinson, B. H.; Dalton, L. R., Benzocyclobutene barrier layer for suppressing conductance in nonlinear optical devices during electric field poling. *Applied Physics Letters* 2014, 104 (24), 243304, the disclosure of which is incorporated herein by reference). The 2.5x+ improvement in EO activity at a given concentration in a polymer host demonstrates the utility of the exemplary chromophores comprising the novel thienothiophene-derived donor such as exemplary Compounds I, II, III, and IV for electro-optic devices, enabling high device performance while providing substantial flexibility for blending with chromophores.

Figure 6A:
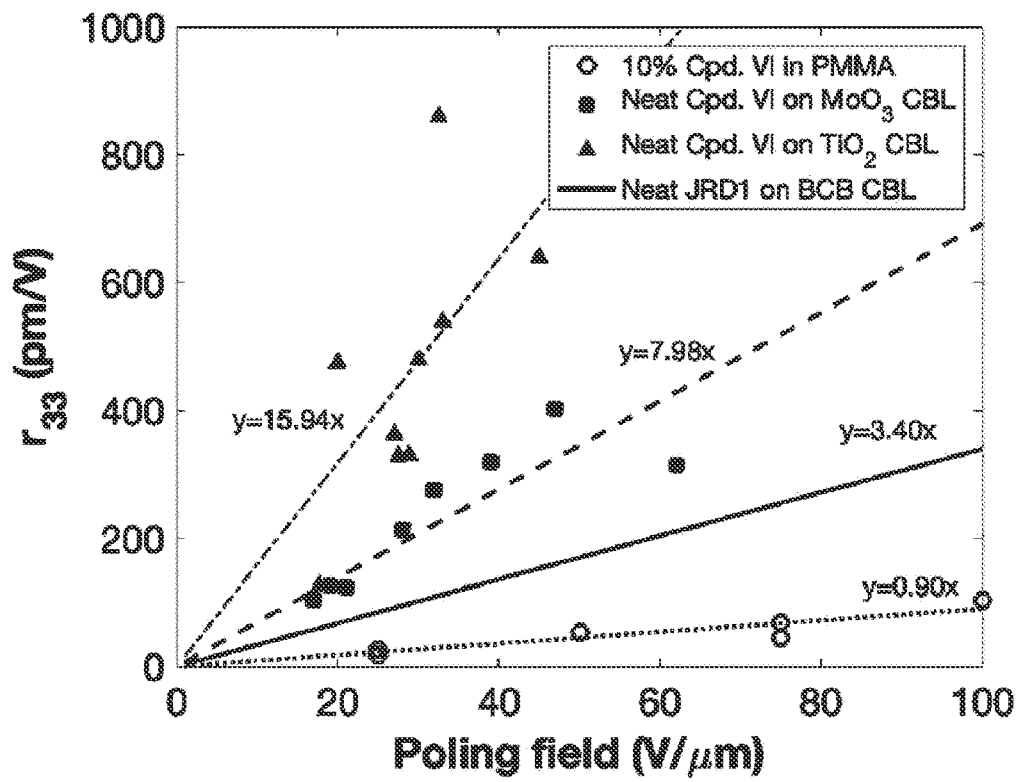
FIGS. 6A and 6B depicts the poling efficiency (electro-optic coefficient as a function of poling field) for exemplary Compound VI under various conditions (FIG. 6A) and the real (n) and imaginary (k) components of the refractive index for exemplary Compound VI (FIG. 6B).
Figure 6B:
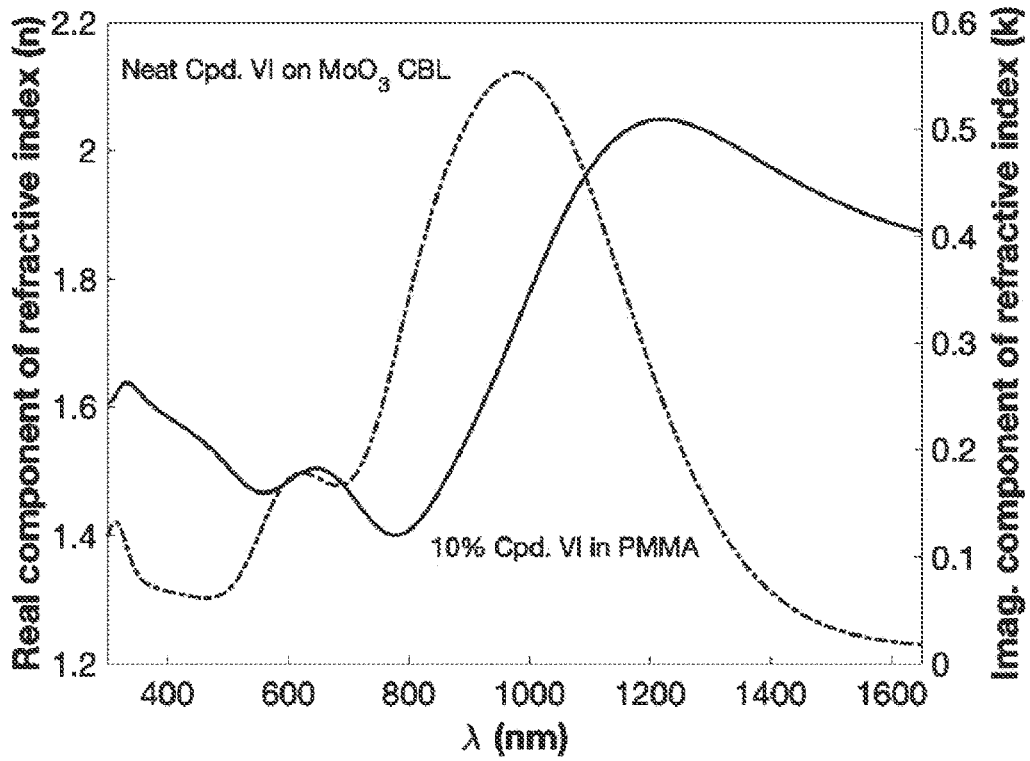

Exemplary Compounds V, VI, and VII showed a range of structural variants of the invention utilizing different aromatic groups and side-chain substitutions in the electron-donating region of the molecule, which allow desired substitutions and tuning of optical properties while demonstrating an improvement in hyperpolarizability over state-of-the-art compound JRD1, as shown in Table 1. Exemplary Compound VI shows competitive poling efficiency at 10% concentration in PMMA (0.90 nm$^2$/V$^2$) to 25% JRD1 in PMMA, and exceptional poling efficiencies as a neat material (100% concentration, no polymer) when combined with a charge blocking layer to reduce current during poling. A poling efficiency of 7.98 was obtained in combination with a MoO$_3$ (20 nm thick, deposited via evaporation) charge blocking layer; a poling efficiency of 15.98 was obtained with a sol-gel TiO$_2$ charge blocking layer. The latter has led to $r_{33}$ values in excess of 600 pm/V, substantially exceeding the record value for JRD1 and exceeding the poling efficiency of JRD1 by nearly a factor of 5. The real component of the refractive index of exemplary Compound VI is also enhanced, reaching values of 2.02 at 1310 nm and 1.90 at 1550 nm, enabling exceptional $n^3 r_{33}$ values. Refractive index and poling data for Compound VI is shown in FIG. 6. Exemplary Compound VII demonstrated a poling efficiency of 0.94 $nm^2/V^2$ at 10% concentration in PMMA, slightly exceeding that of 10% exemplary Compound VI in PMMA.

While illustrative embodiments have been illustrated and described, it will be appreciated that various changes can be made therein without departing from the spirit and scope of the invention.

The invention claimed is:

1. A compound of formula:

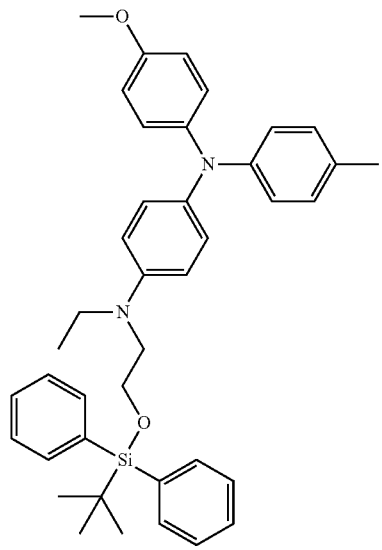

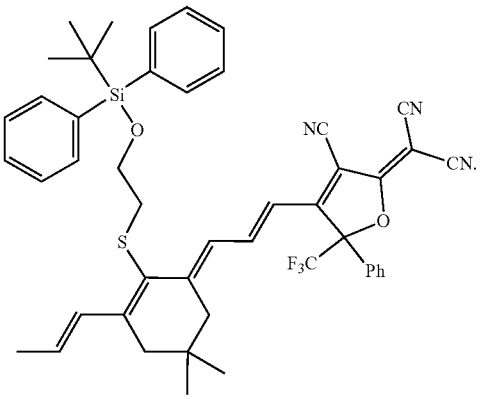

2. A film having electro-optic activity comprising compound of claim 1.

3. A method for forming a film having electro-optic activity, comprising depositing the compound of claim 1 on a substrate to provide a film, applying an aligning force to the film at a temperature sufficient to provide a film having a portion of the compound aligned, and reducing the temperature of the film to provide a film having electro-optic activity.

4. An electro-optic device comprising a compound of claim 1.

5. The electro-optic device of claim 4, wherein the device is an electro-optic modulator, antenna, Mach-Zehnder modulator, phase modulator, silicon-organic hybrid modulator, plasmonic-organic hybrid modulator, electrical-to-optical convertor, terahertz detector, frequency shifter, or frequency comb source.

* * * * *